(12) United States Patent
Hee-Hanson et al.

(10) Patent No.: US 12,274,872 B1
(45) Date of Patent: Apr. 15, 2025

(54) COLLAR HOLD DETENT MECHANISM AND LOCK FOR INJECTION DEVICES

(71) Applicant: Genzyme Corporation, Cambridge, MA (US)

(72) Inventors: Alexander Hee-Hanson, Melbourn (GB); Thomas Lever, Melbourn (GB); Michael Parrott, Melbourn (GB); Robert Wilson, Melbourn (GB)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 18/620,097

(22) Filed: Mar. 28, 2024

(51) Int. Cl.
*A61M 5/32* (2006.01)

(52) U.S. Cl.
CPC ............. *A61M 5/322* (2013.01); *A61M 5/326* (2013.01); *A61M 2005/3267* (2013.01); *A61M 5/3271* (2013.01)

(58) Field of Classification Search
CPC ................ A61M 5/326; A61M 5/3243; A61M 2005/3247; A61M 5/3271; A61M 2005/3267
See application file for complete search history.

(56) References Cited

U.S. PATENT DOCUMENTS

| 4,900,311 A | 2/1990 | Stern et al. |
| 5,088,986 A | 2/1992 | Nusbaum |

(Continued)

FOREIGN PATENT DOCUMENTS

| WO | WO 2011/123024 A1 | 10/2011 |
| WO | WO 2014/115241 A1 | 7/2014 |

(Continued)

OTHER PUBLICATIONS

Needle-based injection systems for medical use requirements and test methods, Part 1: Needle injection systems, ISO 11608-1:2014(E), Third Edition, Switzerland, ISO, Dec. 15, 2014, pp. 1-13.

(Continued)

*Primary Examiner* — Laura A Bouchelle
(74) *Attorney, Agent, or Firm* — Fish & Richardson P.C.

(57) ABSTRACT

This application relates to an injector device for delivery of a medicament, particularly to an auto-injector device. According to a first aspect of this disclosure, there is described an injection device comprising: an injection device body; a needle shroud retractable into the injection device body comprising a shroud pin; a control spring coupled to the needle shroud and biased to cause the needle shroud to be at least partially extended from the injection device body in an initial position; and a collar rotatable with respect to the injection device body and comprising a cam track engageable with the shroud pin; a hold detent mechanism coupled to the cam track of the collar, wherein the hold detent mechanism is configured to: activate, when the needle shroud is retracted from a first position on the cam track into the injection device body to a hold position on the cam track, by engaging the shroud pin thereby creating a hold detent force opposite a control spring force caused by compression of the control spring during said retraction of needle shroud to said hold position; and deactivate, when the needle shroud is extracted from the hold position on the cam track subsequent to the retraction towards a second position on the cam track, by disengaging the shroud pin thereby releasing the hold detent force and enable the needle shroud to extend from the injection device body to the second position on the cam track; and wherein the hold detent mechanism further comprises a non-return surface configured to, subsequent to (Continued)

the extension of the needle shroud, prevent further retraction of the needle shroud into the injection device body along the cam track towards the hold position.

27 Claims, 14 Drawing Sheets

(56) References Cited

U.S. PATENT DOCUMENTS

| | | | |
|---|---|---|---|
| 5,290,256 | A | 3/1994 | Weatherford et al. |
| 5,688,241 | A | 11/1997 | Asbaghi |
| 7,597,685 | B2 | 10/2009 | Olson |
| 8,016,797 | B2 * | 9/2011 | Gratwohl .............. A61M 5/326 604/171 |
| 8,821,451 | B2 | 9/2014 | Daniel |
| 9,199,038 | B2 | 12/2015 | Daniel |
| 9,408,976 | B2 | 8/2016 | Olson et al. |
| 9,498,579 | B2 * | 11/2016 | Ruan ................... A61M 5/3257 |
| 9,662,452 | B2 | 5/2017 | Daniel |
| 9,867,940 | B2 | 1/2018 | Holmqvist et al. |
| 9,919,107 | B2 * | 3/2018 | Imai ...................... A61M 5/326 |
| 10,420,898 | B2 | 9/2019 | Daniel |
| 11,369,751 | B2 * | 6/2022 | Ruan ................... A61M 5/3272 |
| 11,944,787 | B2 | 4/2024 | Franke |
| 2006/0276756 | A1 | 12/2006 | Francavilla |
| 2010/0268170 | A1 | 10/2010 | Carrel et al. |
| 2012/0203186 | A1 | 8/2012 | Vogt et al. |
| 2013/0041328 | A1 | 2/2013 | Daniel |
| 2013/0096512 | A1 | 4/2013 | Ekan et al. |
| 2013/0123710 | A1 | 5/2013 | Ekman et al. |
| 2013/0261559 | A1 | 10/2013 | Werbickas |
| 2014/0025013 | A1 | 1/2014 | Dowds et al. |
| 2015/0190580 | A1 | 7/2015 | Imai et al. |
| 2015/0258283 | A1 | 9/2015 | Imai et al. |
| 2016/0089498 | A1 | 3/2016 | Daniel |
| 2018/0064875 | A1 | 3/2018 | Holmqvist |
| 2018/0361082 | A1 | 12/2018 | Sall et al. |
| 2020/0289755 | A1 | 9/2020 | Franke |
| 2021/0236732 | A1 | 8/2021 | Chu et al. |
| 2021/0244887 | A1 | 8/2021 | Halseth |
| 2021/0393886 | A1 | 12/2021 | Nicolas et al. |
| 2022/0387719 | A1 | 12/2022 | Wang et al. |
| 2022/0395642 | A1 | 12/2022 | Karlsson |
| 2024/0139430 | A1 | 5/2024 | Chansavang et al. |
| 2024/0165346 | A1 | 5/2024 | Chansavang et al. |

FOREIGN PATENT DOCUMENTS

| | | |
|---|---|---|
| WO | WO 2021/008839 A1 | 1/2021 |
| WO | WO 2023/104512 A1 | 6/2023 |

OTHER PUBLICATIONS

U.S. Appl. No. 18/619,754, filed Mar. 28, 2024, Alexander Hee-Hanson.

U.S. Appl. No. 18/619,991, filed Mar. 28, 2024, Alexander Hee-Hanson.

U.S. Appl. No. 18/620,210, filed Mar. 28, 2024, Alexander Hee-Hanson.

U.S. Appl. No. 18/620,586, filed Mar. 28, 2024, Alexander Hee-Hanson.

U.S. Appl. No. 18/619,996, filed Mar. 28, 2024, Alexander Hee-Hanson.

* cited by examiner

COLLAR HOLD DETENT MECHANISM AND LOCK FOR INJECTION DEVICES

FIELD OF THE INVENTION

This application relates to an injector device for delivery of a medicament, particularly to an auto-injector device.

BACKGROUND

An auto-injector may be described as a device which completely or partially replaces the activities involved in parenteral drug delivery from a standard syringe. Typically, these include removal of the protective syringe cap, insertion of the needle, injection of drug and possibly removal and shielding of the used needle. Administering an injection is a process which presents several risks and challenges, both mental and physical. The use of an auto-injector can bring many benefits for the user and healthcare professional.

Many auto-injectors have a needle cover which is biased by a spring (the needle cover spring) to extend out of the device. On removal of the device from the injection site, this spring automatically extends the needle cover past the needle to provide needle shielding. On activation of the device, the needle cover is pushed into the device. A user has to provide the force to actuate the needle cover, overcome the activation mechanism forces and compress the needle cover spring (activation force). More importantly, during drug delivery the user must hold the device at the injection site and apply a force (hold force) parallel to the needle cover direction of extension to react the needle cover biasing member.

If the activation or hold force is too high or has a certain profile, it can lead to use issues such as incorrectly thinking the device is not working, inadvertent early removal or a wet injection site. Some users have difficulty applying this hold force during the full drug delivery time. This results in pain, discomfort, a wet injection site, early device removal and partial drug delivery. Furthermore, on device removal

SUMMARY

According to a first aspect of this disclosure, there is described an injection device comprising: an injection device body; a needle shroud retractable into the injection device body comprising a shroud pin; a control spring coupled to the needle shroud and biased to cause the needle shroud to be at least partially extended from the injection device body in an initial position; and a collar rotatable with respect to the injection device body and comprising a cam track engageable with the shroud pin; a hold detent mechanism coupled to the cam track of the collar, wherein the hold detent mechanism is configured to: activate, when the needle shroud is retracted from a first position on the cam track into the injection device body to a hold position on the cam track, by engaging the shroud pin thereby creating a hold detent force opposite a control spring force caused by compression of the control spring during said retraction of needle shroud to said hold position; and deactivate, when the needle shroud is extracted from the hold position on the cam track subsequent to the retraction towards a second position on the cam track, by disengaging the shroud pin thereby releasing the hold detent force and enable the needle shroud to extend from the injection device body to the second position on the cam track; and wherein the hold detent mechanism further comprises a non-return surface configured to, subsequent to the extension of the needle shroud, prevent further retraction of the needle shroud into the injection device body along the cam track towards the hold position.

The injection device, where the hold detent mechanism may comprise a hold detent feature coupled to the collar, which, when activated, interacts with the shroud pin for creating the hold detent force.

The injection device, where the hold detent feature may further comprise at least one of: a flexible arm; a resilient clip; a high friction interface; partial cut-out or flap on the needle shroud; any other member or mechanism for engaging the shroud pin and creating a hold detent force opposite the control spring force caused by compression of the control spring during said retraction of needle shroud to said hold position.

The injection device, where the cam track may comprise: a first portion of the cam track configured to, during retraction of the needle shroud into the injection device body, guide the shroud pin from the first position to the hold position and cause the collar to rotate relative to the injection device body; a second portion of the cam track configured to, during extension of the needle shroud from the injection device body subsequent to the retraction, guide the shroud pin from the hold position to the second position; wherein the hold detent mechanism is positioned in a region of intersection between the first and second portions of the cam track, and is further configured to guide the shroud pin towards the hold position prior to activating.

The injection device, where the hold detent feature may further comprise a first ramped wall surface for guiding the shroud pin from the first portion of the cam track to the second portion of the cam track towards the hold position.

The injection device, where the hold detent feature may further comprise a second ramped contact surface that intersects with the first ramped wall surface and configured for engaging with the shroud pin in the region of intersection of the first and second portions of the cam track after needle shroud is retracted to the hold position and prior to retraction, wherein the hold detent mechanism activates by the second ramped contact surface engaging with at least a portion of the shroud pin causing a hold detent force in an opposite direction to the control spring force caused by compression of the control spring during retraction.

The injection device, where when the needle shroud is extracted from the hold position subsequent to the retraction, the hold detent mechanism is deactivated by the control spring force overcoming the hold detent force in which the shroud pin is guided by the second portion of the cam track to pass over the second ramped contact face of the hold detent feature to create a biasing force on a portion of the hold detent feature that radially flexes the portion of the hold detent feature away from the shroud pin towards the longitudinal axis of the injection device body or collar enabling the control spring force to extract the needle shroud to substantially the second position.

The injection device, where the portion of the hold detent feature that has a biasing force applied to radially flex away from the shroud pin towards the longitudinal axis of the injection device body or collar is the non-return surface of the hold detent feature, and when the shroud pin is guided along the second portion of the cam track past the non-return surface of the hold detent feature, the biassing force is released causing the portion of the hold detent feature to radially flex towards is original configuration, wherein the non-return surface when the hold detent feature is in the original configuration prevents further retraction of the needle shroud into the injection device body along the second portion of cam track towards the hold position.

The injection device, where the first hold detent feature is coupled to the collar shroud by a snap fit.

The injection device, where the first hold detent feature is integral to the collar and formed by a resilient partial cut-out of the collar.

The injection device, where the hold detent force of the hold detent mechanism at least partially supports the needle shroud against the control spring force rather than the full control spring force being fully transferred to the user when the injection device is in the hold position.

The injection device, where the control spring is a compression spring configured to bias the needle shroud towards an extended position.

The injection device further comprising: a plunger and biasing means for biasing the plunger towards the distal end of the injection device, wherein: when the needle shroud is in the first position, the plunger is retained by a combination of the rear casing and the collar preventing the biasing means from displacing the plunger in the distal direction; and on activation of the injection device, the collar rotates and guides the shroud pin of the needle shroud to the holding position and causing, when the needle shroud is in the holding position, the biasing means to move the plunger in the distal direction of the injection device.

The injection device further comprising a needle, and wherein the needle shroud is arranged to shroud the needle when in an extended position.

The injection device further comprising a reservoir containing a medicament, the reservoir coupled to the plunger via a stopper at a distal portion of the reservoir and the reservoir coupled to the needle at a proximal end of the reservoir, and wherein, when the needle shroud moves into the holding position, the biasing means moves the plunger to displace the stopper in the distal direction causing the medicament stored in the reservoir to be expelled from the injection device via the needle.

The injection device further comprising at least two hold detent mechanisms equally spaced around the circumference of the collar.

According to a second aspect of this specification, there is described a collar for an injection device comprising a cam track engageable with a shroud pin of a needle shroud and a hold detent mechanism coupled to the cam track of the collar, wherein: the needle shroud is retractable into the injection device body of the injection device, the injection device comprising a control spring coupled to the needle shroud and biased to cause the needle shroud to be at least partially extended from the injection device body in an initial position; the collar is rotatable in relation to the longitudinal axis of the injection device body; and the hold detent mechanism is configured to: activate, when the needle shroud is retracted from a first position on the cam track into the injection device body to a hold position on the cam track, by engaging the shroud pin thereby creating a hold detent force opposite a control spring force caused by compression of the control spring during said retraction of needle shroud to said hold position; and deactivate, when the needle shroud is extracted from the hold position on the cam track subsequent to the retraction towards a second position on the cam track, by disengaging the shroud pin thereby releasing the hold detent force and enable the needle shroud to extend from the injection device body to the second position on the cam track; and wherein the hold detent mechanism further comprises a non-return surface configured to, subsequent to the extension of the needle shroud, prevent further retraction of the needle shroud into the injection device body along the cam track towards the hold position.

The collar, wherein the hold detent mechanism comprises a hold detent feature coupled to the collar, which, when activated, interacts with the shroud pin for creating the hold detent force.

The collar, wherein the hold detent feature comprises at least one of: a flexible arm; a resilient clip; a high friction interface; partial cut-out or flap on the needle shroud; any other member or mechanism for engaging the shroud pin and creating a hold detent force opposite the control spring force caused by compression of the control spring during said retraction of needle shroud to said hold position.

The collar, wherein the cam track comprises: a first portion of the cam track configured to, during retraction of the needle shroud into the injection device body, guide the shroud pin from the first position to the hold position and cause the collar to rotate relative to the injection device body; a second portion of the cam track configured to, during extension of the needle shroud from the injection device body subsequent to the retraction, guide the shroud pin from the hold position to the second position; wherein the hold detent mechanism is positioned in a region of intersection between the first and second portions of the cam track, and is further configured to guide the shroud pin towards the hold position prior to activating.

The collar, wherein the hold detent feature comprises a first ramped wall surface for guiding the shroud pin from the first portion of the cam track to the second portion of the cam track towards the hold position.

The collar, wherein the hold detent feature comprises a second ramped contact surface that intersects with the first ramped wall surface and configured for engaging with the shroud pin in the region of intersection of the first and second portions of the cam track after needle shroud is retracted to the hold position and prior to retraction, wherein the hold detent mechanism activates by the second ramped contact surface engaging with at least a portion of the shroud pin causing a hold detent force in an opposite direction to the control spring force caused by compression of the control spring during retraction.

The collar, wherein when the needle shroud is extracted from the hold position subsequent to the retraction, the hold detent mechanism is deactivated by the control spring force overcoming the hold detent force in which the shroud pin is guided by the second portion of the cam track to pass over the second ramped contact face of the hold detent feature to create a biasing force on a portion of the hold detent feature that radially flexes the portion of the hold detent feature away from the shroud pin towards the longitudinal axis of the injection device body or collar enabling the control spring force to extract the needle shroud to substantially the second position.

The collar, wherein the portion of the hold detent feature that has a biasing force applied to radially flex away from the shroud pin towards the longitudinal axis of the collar is the non-return surface of the hold detent feature, and when the shroud pin is guided along the second portion of the cam track past the non-return surface of the hold detent feature, the biassing force is released causing the portion of the hold detent feature to radially flex towards is original configuration, wherein the non-return surface when the hold detent feature is in the original configuration prevents further retraction of the needle shroud into the injection device body along the second portion of cam track towards the hold position.

The collar, wherein the first hold detent feature is coupled to the collar shroud by a snap fit.

The collar, wherein the first hold detent feature is integral to the collar and formed by a resilient partial cut-out of the collar.

The collar, wherein the hold detent force of the hold detent mechanism at least partially supports the needle shroud against the control spring force rather than the full control spring force being fully transferred to the user when the injection device is in the hold position.

The collar, wherein the control spring is a compression spring configured to bias the needle shroud towards an extended position.

According to a further aspect of this specification, there is described a method for reducing the holding force of a needle shroud of an injection device during use, the method comprising: during retraction of the needle shroud from a first position along a cam track of a collar into an injection device body, activating a hold detent mechanism coupled to the collar when the needle shroud retracts to a hold position on the cam track by engaging a shroud pin on the needle shroud thereby creating a hold detent force opposite a control spring force caused by compression of a control spring coupled to the needle shroud during said retraction of needle shroud to said hold position; during extension of the needle shroud from the hold position on the cam track subsequent to the retraction towards a second position on the cam track, deactivating the hold detent mechanism when the needle shroud extends from the hold position to the second position by disengaging the shroud pin to release the hold detent force and enable the needle shroud to extend from the injection device body to substantially the second position on the cam track; and subsequent to the extension of the needle shroud, preventing further retraction of the needle shroud into the injection device body along the cam track using a non-return surface on the hold detent mechanism.

Throughout this specification, use of the injection device is described in terms of a user, who operates the injection device, and a subject, who receives an injection from the injection device. The user and the subject may be the same person. Alternatively, the user and subject may be different entities, e.g., a healthcare provider and a patient or a vet/farmer and a pet/animal.

BRIEF DESCRIPTION OF THE DRAWINGS

Exemplary embodiments of the present invention are described with reference to the accompanying drawings, in which.

DETAILED DESCRIPTION

Figure 1:
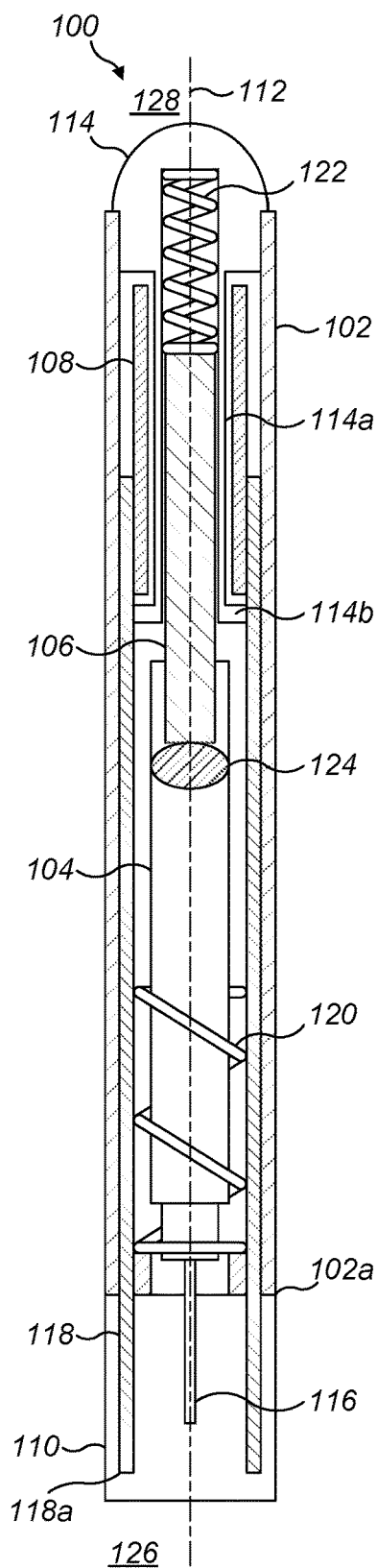
FIG. 1 shows a schematic example of a cross section of an injection device.

A drug delivery device, as described herein, may be configured to inject a medicament into a subject. For example, delivery could be sub-cutaneous, intra-muscular, or intravenous. Such a device could be operated by a subject or other user (e.g., a care-giver, such as a nurse or physician), and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a subject's skin for a period of time (e.g., about 5, 15, 30, 60, or 120 minutes) to deliver a "large" volume of medicament (typically about 2 ml to about 10 ml). The subject may include, without limitation, for example a person, a patient, a human, a mammal, a pet, or animal and/or any other suitable subject that requires a dosage of a medicament delivered by the injection device. The subject may be, without limitation, for example the user or operator of the injection device (e.g., a person self-administering a medicament). The user may include, without limitation, for example an operator of the device, a person, a care-giver, nurse, physician, vet, a robotic arm, or appendage configured for delivering a medicament via the injection device under remote control and/or automatic operation, a subject (e.g., self-administering the medicament via the injection device) and the liked.

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 27 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body or a subject's body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Auto-injectors require user actions to commence drug delivery. One of these actions apply an axial force to the device by either pushing a needle shroud (or needle cover) into the device or pressing a button on the device. The axial force required is referred to as the activation force or control spring force in this document. The magnitude and profile of this activation force (or control spring force) and also, after activation, the magnitude and profile of the holding force required to hold the device at the injection site until the medicament is delivered has an impact on the usability of the device.

During activation, the user must react the control spring force during activation and hold for a period of time to ensure the correct dosage of medicament is delivered. It may be beneficial to reduce the hold and/or activation force. Reducing the force to activate the needle cover locking mechanism, enables a reduction in the control spring and therefore reduces the hold and activation forces. Moreover, reducing the force to hold the device and needle at the injection site whilst for delivering the medicament, reduces the energy or hold force required by a user and/or automatic holding mechanism in overcoming the opposing forces of the control spring and therefore reduces the hold forces required to operate the injection device. This can reduce the effort in applying the hold force during delivery of the medicament for the full drug delivery time, which may further reduce pain and/or discomfort for the subject and/or user whilst improving the correct working and operation of the injection device to ensure that the medicament is fully delivered to the subject.

After the device is removed from the subject's body post use, many autoinjectors cover the needle with a shroud/needle cover, which is extended out of the device by a control spring. This shroud is locked in its extended position by a needle cover locking mechanism, often featuring a one-way clip feature. The control spring must have enough force to ensure this mechanism is activated following device removal and the needle is enclosed to allow safe disposal.

Injection devices described herein use a hold detent mechanism for lowering the holding force to the user of the device for delivering the medicament. The injection device described herein comprises a hold detent mechanism that is coupled to at least the collar used for guiding the needle shroud of the injection device from an initial position to the hold position and then, a subsequent final or locked position. For example, the hold detent mechanism may be coupled to the collar and interact with the needle shroud of the injection device. The collar has a cam track configured to, when the collar is activated and rotatable, engage with the needle shroud to rotate the collar and guide the needle shroud to move from the initial position to the hold position. This rotation of the collar may activate, once the needle shroud is in the hold position, a plunger in the injection device to deliver the medicament to the subject. Once the medicament has been delivered, the cam track of the collar may engage and/or guide the needle shroud to the final position, which may lock the needle shroud in an extended position to cover the needle.

The hold detent mechanism is positioned on the cam track such that it assists in guiding the needle shroud to the hold position, and then activates to provide a hold force that is opposite a control spring force caused by compression of a control spring used during said retraction of needle shroud to said hold position. This can assist a user to apply less hold force to maintain the needle shroud in the hold position when the medicament is being delivered. When activated the hold detent mechanism engages with a portion of the needle shroud to provide a hold force opposite the control spring force. When the medicament is delivered, the user may release their hold force in which the hold detent mechanism deactivates and releases the hold detent force such that the control spring force enables the needle shroud to be guided by the cam track and extracted from the hold position to extend from the injection device body to a final position or locked position. The hold detent mechanism after deactivation may have a non-return surface that locks the needle shroud into the extracted state, i.e., final position or locked position. In the final position or locked position, the needle shroud substantially covers or encloses the needle of the injection device for safe disposal of the device.

The force used to maintain the needle shroud in the hold position is less than the force required to maintain the hold position on many auto-injector needle cover mechanisms, resulting in a reduction in user hold force during delivery of the medicament to the subject.

FIG. 1 shows a schematic example of a cross section of an injection device 100. The injection device is configured to inject a medicament into a subject's body. The injection device 100 comprises an outer casing 102 that encloses a reservoir 104, a plunger 106 and a rotatable collar 108. The reservoir 104 typically contains the medicament to be injected, and may, for example, be in the form of a syringe. The injection device 100 can also include a cap assembly 110 that can be detachably mounted to the outer casing 102. Typically a user must remove cap 110 from the outer casing 102 before device 100 can be operated.

As shown, casing 102 is substantially cylindrical and has a substantially constant diameter along the longitudinal axis 112 of the device 100. The injection device 100 has a distal region and a proximal region. The term "distal" refers to a location that is relatively closer to a site of injection on the subject, which is illustrated in FIG. 1 as distal end 126 of the injection device 100, and the term "proximal" refers to a location that is relatively further away from the injection site, which is illustrated in FIG. 1 as proximal end 128 of the injection device 100 or typically the rear casing 114 from which the user may apply the activation and user hold forces. The outer casing 102 is closed at the proximal end 128 by the rear casing 114. The rear casing 114 may further include a rear casing sheaf 114*a* and rear casing sheaf end stop 114*b* for rotatably coupling to the collar 108 and maintaining the vertical position of the collar 108 within the body or outer casing 102 of the injection device 100. In some embodiments, the rear casing sheaf 114*a* may be, without limitation, for example a rear casing collar bearing surface 114*a* or other surface or structure suitable for rotatably coupling to the collar 108. Alternatively or additionally, the rear casing 114 may include a rear casing collar bearing surface 114*a* for rotatably coupling to the collar 108 and a rear casing collar end stop 114*b* for maintaining the vertical position of the collar 108 within the body or outer casing 102 of the injection device 100.

A needle 116 and a retractable needle shroud 118 (also referred to as a "needle sleeve" or "needle cover") extend from a distal end 102*a* of the outer casing 102. The retractable needle shroud 118 is biased in the distal direction of the injection device 100, for example using a control spring 120. The needle shroud 118 is coupled to the outer casing 102 to permit movement of needle shroud 118 relative to the outer casing 102. For example, the shroud 118 can move in a longitudinal direction parallel to longitudinal axis 112. The needle shroud 118 is coupled in the vicinity of the proximal end of the needle shroud 118 to the collar 108 (e.g., via cam tracks in the collar 108), which is configured to rotate as the needle shroud 118 is guided (e.g., via the cam tracks) in a proximal direction from an initial position as depicted in FIG. 1 to a retracted position or hold position in which the distal end 118*a* of the needle shroud 118 is substantially flush with the distal end 102*a* of the outer casing 102. Specifically, movement of needle shroud 118 in the proximal direction substantially parallel to the longitudinal axis 112 of the outer casing 102 can permit a needle 116 to extend from the distal end of the outer casing 102.

The plunger 106 is biased towards the distal end 126 of the injection device 100 by a biasing means, for example using a drive spring 122. The plunger 106 is retained in an initial position by a combination of the rear casing 114 and the collar 108, preventing the biasing means from displacing the plunger 106 in the distal direction. Activation of the injection device 100 and engagement of needle shroud 118 with collar 108 (e.g., via cam tracks on the collar) causes the collar 108 to rotate which releases the plunger 106 once needle shroud 118 is in the hold position. Once in the hold position and the plunger 106 is released, the biasing means causes the plunger 106 to move in the distal direction (i.e., towards the needle 116 end of the injection device 100). The plunger 106 contacts a stopper 124 in the reservoir 104, displacing the stopper 124 in the distal direction and causing medicament stored in the reservoir 104 to be expelled from the injection device 100 via the needle 116.

Activation of the injection device 100 by a user can occur via several mechanisms. For example, the needle 116 may be fixedly located relative to the outer casing 102 and initially be located within an extended needle shroud 118. That is the needle 116 is enclosed by the needle shroud 118 as depicted in FIG. 1. Proximal movement of shroud 118 by placing a distal end 118*a* of the needle shroud 118 against a subject's body and the user applying an activation force (e.g., the activation force may be applied via the rear casing 114 or by user holding the outer casing 102 and applying force longitudinally towards the distal end 126 of the injection device 100) that moves outer casing 102 in a distal direction will uncover the distal end of the needle 116. Such relative movement allows the distal end of the needle 116 to extend into the subject's body. Such insertion is termed "manual" insertion as the needle 116 is manually inserted via the user's manual movement of the outer casing 102 relative to needle shroud 118. Retraction of the needle shroud 118 into the outer casing 102 causes the collar 108 to rotate, releasing the plunger 106.

Another form of activation is "automated," whereby the needle 116 moves relative to casing 102. Such insertion can be triggered by movement of the needle shroud 118 and/or by another form of activation, such as, for example, a button (not shown).

Typically, the user presses the needle shroud 118 against an injection site to push the needle shroud 118 at least partially into the device body. The exposed needle 116 is pushed into the injection site. In a holding position, medicament is automatically dispensed from the needle 116 via an automated mechanism. However, a user must typically hold the needle shroud 118 in the holding position against the patient's body for a predetermined period of time, to ensure that the correct dose of medicament is dispensed from the device 100, before removing the device from the injection site.

The spring force from the control spring 120 against which the user must apply a force to move the needle shroud 118 is one component of an "activation force" of the device 100. The activation force refers to the force or force profile that the user must exert on the device 100 to move the needle shroud 118 from the extended position shown in FIG. 1 to a retracted position. If this force or force profile is not well balanced, it can lead to difficulty in activating the injection device 100 for some users, or increase the pain or anxiety associated with using the injection device 100.

Furthermore, once activated and the needle shroud 118 is in its retracted position, the user must continue to apply a "holding force" to counteract the spring force from the control spring 120 to keep the needle 116 pushed into the injection site whilst minimising any movement that may cause further pain or discomfort to the subject whilst medicament from reservoir 104 is delivered. The holding force refers to the force or force profile that the user must exert on the injection device 100 to maintain the needle shroud 118 in the retracted position and keep the needle 116 pushed into the injection site for fully delivering the medicament. If this force or force profile is not well balanced, it can lead to difficulty in administering the correct dosage of medicament to the subject and increase the likelihood of pain and/or discomfort to the subject, and/or increase the user's anxiety associated with using the injection device 100.

Following injection, the injection device 100 may be moved proximally from the injection site to remove needle 116 from subject's body in which the needle 116 is automatically retracted within the needle shroud 118 to substantially a distal position similar to its starting position as depicted in FIG. 1. Retraction can occur when the shroud 118 moves distally under the biasing of the control spring 120 as a user removes the device 100 from a subject's body. Once a distal end of needle shroud 118 has moved past a distal end of the needle 116, and the needle 116 is covered, the needle shroud 118 is locked. Such locking can include locking any (substantial) proximal movement of the needle shroud 118 relative to the outer casing 102, i.e., to prevent any movement of the needle shroud 118 that would uncover the needle 116.

FIGS. 2A-2F shows an example of the operation of a hold detent mechanism 202 coupled to a needle shroud 204 and injection device body or outer casing 206. The needle shroud 204 and injection device body or outer casing 204 and rear casing 206 correspond to the needle shroud 118 and outer casing 102 and rear casing 114 of FIG. 1, but which are further modified to include hold detent mechanism 210.

Figure 2A:
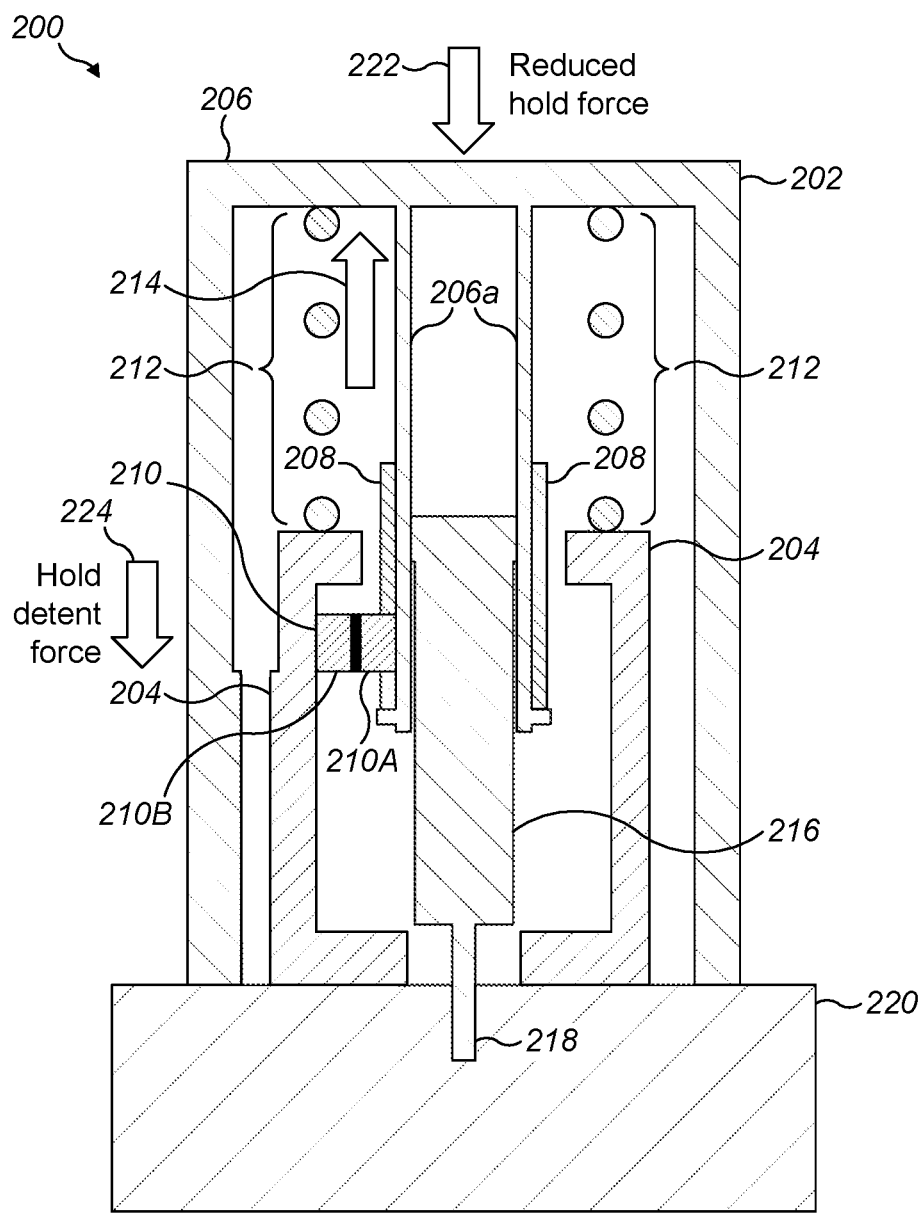
FIG. 2A shows a schematic example of a cross section of an injection device with a hold detent mechanism.

FIG. 2A shows an example of an injection device 200 with a hold detent mechanism 210 coupled to a needle shroud 204 and a collar 208, e.g., the injection device of FIG. 1. The injection device 200 includes an injection device body or outer casing 202 with a rear casing 206 within which the needle shroud 204 is retractably mounted. The needle shroud 204 is configured to be retractable into the injection device body or outer casing 204. A control spring 212 is coupled to the needle shroud 204 within the injection device body or outer casing 202 and rear casing 206. The control spring 212 (e.g., a compression spring) is biased to cause the needle shroud 204 to be at least partially extended from the injection device body or outer casing 202 when in an initial position (e.g., as shown in FIG. 1) in which the needle shroud 204 is extended out from the injection device body or outer casing 202 and at least fully covers or encloses the needle 218. Thus, the injection device 200 has a distal end in which the needle shroud 204 extends outside the injection device body or outer casing 202 at the initial position. The rear casing 206 may be coupled to rear casing sheaf 206a, which longitudinally extends into the injection device 200 to rotatably secure the collar 208 in place, e.g., prevent excessive longitudinal movement along the axis of the injection device body or outer casing 202 when in operation. The injection device 200 further includes a reservoir 216 coupled to a needle 218 at a distal end of the injection device body or outer casing 202.

As depicted in FIG. 2A, a user has already placed the distal end of the injection device 200 (i.e., the distal end of the extended portion of the needle shroud 204) on an injection site of a subject 220 and has also applied an axial hold force 222 to the proximal end of the rear casing 206 of the outer casing 202 and along the longitudinal axis of the injection device 200 causing the needle shroud 204 to retract into the injection device body or outer casing 202. The user has applied enough axial hold force 222 to enable the needle shroud 204 to be retracted into the injection device body or outer casing 202 whilst compressing the control spring 212. During retraction of the needle shroud 204, the needle 218 is exposed and, in this example, enters the subject 220. The control spring 212 exerts a control spring force 214 that is in an opposite direction to the hold force 222 as the user forces the needle shroud 204 to be retracted into the injection device body or outer casing 202 until a hold position is reached. In this example, the hold position is reached when the needle shroud 204 is substantially flush with the distal end of the injection device body or outer casing 202 as depicted in FIG. 2A.

The hold detent mechanism 210 is coupled to at least the collar 208 via a first hold detent feature 210A of the collar 208 and is configured to engage with a second hold detent feature 210B of the needle shroud 204 as shown in FIG. 2A when the needle shroud 204 has reached the hold position after activation of injection device 200 and retraction of the needle shroud 204. The hold position occurs after the needle shroud 204 has been retracted from the initial position (e.g., as shown in FIG. 1) until distal end of the needle shroud 204 is substantially flush with the distal end of the injection device body or outer casing 202 as depicted in FIG. 2A.

When the hold position is reached as shown in FIG. 2A, the hold detent mechanism 210 is then is activated to create a hold detent force 224 in an opposite direction to the control spring force 214 caused by compression of the control spring 212 during said retraction of needle shroud 204 to said hold position. In this example, the hold detent mechanism 210 includes the first hold detent feature 210A coupled to the collar 208, which, when activated, engages with a second hold detent feature 202B on the needle shroud 204 for creating the hold detent force 220. In this case, the hold force 222 of the user (or user hold force) reduces by an amount substantially equal to the hold detent force 224. This provides the advantage that the user exerts less effort to maintain the needle shroud 204 in the hold position while waiting for the required dosage of medicament from the reservoir 216 to be delivered via needle 218 to the subject 220.

When the medicament is delivered, the user may release the applied reduced hold force 222 in which the first and second hold detent features 210A and 210B of the hold dent mechanism 210 deactivate to release the hold detent force 224 and enable (via the control spring 212) the needle shroud 204 to extend from the injection device body or outer casing 202. When the hold detent mechanism 210 is deactivated, the control spring force 214 of the control spring 212 is released and causes the needle shroud 204 to extend from the injection device body or outer casing 202 because the control spring force 214 overcomes the released reduced hold force 222 until the needle shroud 204 substantially reaches the final or locked position. The hold detent mechanism 210 may further include a locking mechanism that prevents any subsequent retraction of the needle shroud 204 into the outer casing 202 that would expose the used needle 218. The locking mechanism may be a non-return surface on the first hold detent feature 210A and/or second hold detent feature 210B of the hold detent mechanism 210, which is configured to lock the needle shroud 204 in the extended position, i.e., a final position or locked position.

Figure 2B:
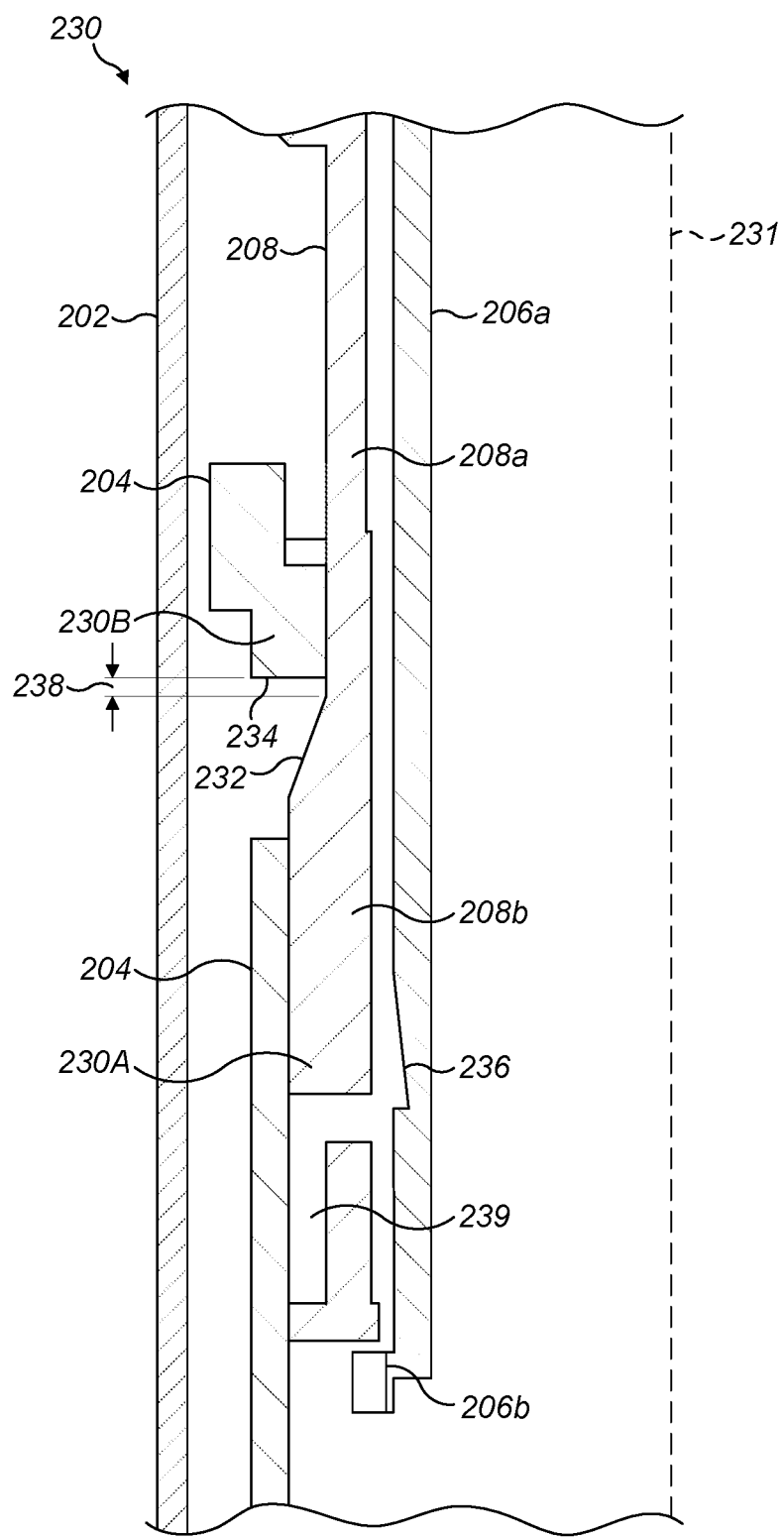
FIG. 2B shows a schematic example of a cross section of a hold detent mechanism for the injection device of FIG. 2A.

FIG. 2B shows an example cross-section schematic of a hold detent mechanism 230 of an injection device that includes first and second hold detent features 230A and 230B when in the hold position prior to activation. For simplicity, reference numerals from FIG. 2A are reused for similar or the same components. In this example, the first hold detent feature 230A is coupled to a flexible arm 208a of the collar 208. The flexible arm 208a forms part of the collar 208 (e.g., a snap fit or integral cut-out). The second hold detent feature 230B (e.g., a shroud pin) is a male component of the needle shroud 204 (e.g., a snap fit or moulded component). The first hold detent feature 230A includes the flexible arm 208a with a ramped surface 232 that starts at a position on the outer surface of the flexible arm 208a of the collar 208 and extends in the direction of the longitudinal axis 231 towards the distal end of the injection device and radially outwardly towards the outer casing 202 to form a thicker non-flexible or less-flexible portion 208b of the flexible arm 208a of the collar 208 that extends in the distal direction and has a substantially uniform thickness. In addition, the rear casing sheaf 206a extends in the distal direction in the direction of the longitudinal axis 231 to a rear casing sheaf end 206b, which is a non-return surface that rotatably secures the collar 208 into position. The rear casing sheaf 206a also has a ramped indented surface or recess 236 that extends radially towards the longitudinal axis 231, and is configured to enable the flexible portion 208a of the collar 208 to be biased and flex the non-flexible portion 208b of the flexible arm 208a of the collar 208 to fill the ramped recess 236 so the second hold detent feature 230B can be guided over the ramped surface 232 of the first hold detent feature 230B as the needle shroud 204 extends from the outer casing 202 to a final or locked position subsequent to the hold position.

In the initial position (not shown), the second hold detent feature 230B (e.g., shroud pin) of the needle shroud 204 when extended from the outer casing 202 is configured to be positioned on the collar 208. On activation of the injection device, the needle shroud 204 is retracted towards the hold position depicted in FIGS. 2A and 2B in which the second hold detent feature 230B is guided by the collar 208 in a proximal direction along the outer surface of the collar 208 (e.g., along a cam track on the collar 208 from initial position to a hold position) until the second hold detent feature 230B locates at a position on the collar 208 that corresponds to the hold position of the injection device, i.e., when the distal end of the needle shroud 204 is substantially flush with the outer casing 202. The collar 208 is configured to guide the second hold detent feature 230B from the initial position to the hold position without contacting ramped surface 232 as the second hold detent feature 230B travels to the hold position as depicted in FIG. 2B. This is to avoid flexing of flexible arm 208a when the second hold detent feature 230B is travelling from the initial position to the hold position. Should the second hold detent feature 230B touch the ramped surface 232 when travelling from the initial position to the hold position, then an increase in the force required by the user is required during injection device activation. This is because an additional friction force caused by the second hold detent feature 230B moving over the ramped surface or at least partially moving over the ramped surface would be required to flex the flexible arm 208a to allow the second hold detent feature 230B to travel to the hold position. Thus, the collar 208 is configured to guide the second hold detent feature 230B from the initial position to the hold position such that the second hold detent feature is prevented from travelling over or hitting the ramped surface 232. The distance 238 may depend in part on the part tolerances of the hold detent mechanism 230, needle shroud 204 and collar 208 and other parts of the injection device but is also large enough to satisfy the requirement that the second hold detent feature 230B is prevented from contacting ramped surface 232 as it travels to the hold position as depicted in FIG. 2B. Once the second hold detent feature 230B is in the hold position, there may be a distance 238 between the distal edge 234 of the second hold detent feature 230B and the point at which the ramped surface meets or intersects with the flexible arm 208a. In this position, the hold detent mechanism 230 is not yet activated because the first hold detent feature 230B is not yet engaged with the second hold detent feature 230A to cause flexing of the flexible arm 208a.

As shown in FIG. 2B, the second hold detent feature 230B is located on the collar 208 in a hold position in which the distal edge 234 of the second hold detent feature 230B of the needle shroud 204 is located in the region where the ramped surface 232 meets the flexible arm 208a of the collar 208 as depicted in FIG. 2B. In this example, the distal edge 234 of the second hold detent feature 230B is a distance 238 from the edge of the ramped surface 232. At this stage in the hold position, the hold detent mechanism 230 is not yet activated. In the current hold position, the second hold detent feature 230B contacts the flexible arm 208a but not the ramped surface 232, so the user hold force is not yet activated the hold detent mechanism 230. The hold detent mechanism 230 is activated when the user slightly reduces the user hold force (e.g., the user may slightly relax their hold force) causing the control spring to extend the needle shroud 204 back out of the outer casing 202 of the injection device to such an extent that the distal edge 234 of the second hold detent feature 230B to engage and contact the ramped surface 232. The hold detent force increases as the distal edge 234 of the second hold detent feature 230B travels, in a distal direction, over the ramped surface 232.

When the hold detent mechanism 230 is activated, the distal edge 234 of the second hold detent feature 230B has engaged with the ramped surface 232 i.e., where the flexible arm 208a of the collar 208 meets the ramped surface 232. This engagement of the distal edge 234 with the ramped surface 232 creates a hold detent force that is equal and opposite to a friction force acting parallel to the longitudinal axis 231 which results from the force required to bias the flexible arm 208a (a resilient material) of the collar 208 such that the flexible arm 208a flexes radially towards the longitudinal axis 231 of the injection device. The beginning of the ramped surface 232 of the first hold detent feature 230A is positioned to enable the hold detent mechanism 230 to activate when the needle shroud 204 travels from the hold position (e.g., the distal end of the needle shroud 204 is substantially flush to the distal end of the outer casing 202) a distance of at least distance 238 in a distal direction towards a final or locked position.

The surface of the male component of the second hold detent feature 230B is configured to be of a size that, for example, reduces friction against the collar 208 as the needle shroud 204 retracts into the outer casing 206 whilst still enabling the needle shroud 204 to retract to the holding position without substantially affecting the required force the user requires to retract the needle shroud 204. Prior to the needle shroud 204 reaching the hold position, the positioning of the second hold detent feature 230B is against the collar 208, which may be guided along a cam track of the collar 208 that guides the second hold detent feature 230B towards the hold position without travelling over the ramped surface 232 so that the second hold detent feature 230B can subsequently engage with the first hold detent feature 230A and activate the hold detent feature 230. The size of the ramped surface 232, the thickness and length of the thicker portion 208b of the flexible arm 208a and also the shape of the second hold detent feature 230B are configured to generate a friction and biassing force that flexes the flexible arm 208a radially away from the outer casing 202 towards the longitudinal axis 231 of the injection device.

As described above, the hold detent force is based, at least in part, on the frictional force caused by the distal edge 234 of the second hold detent feature 230B moving in the distal direction over ramped surface 232 resulting from the biassing force required to radially flex or bias the flexible arm 208a towards the longitudinal axis 231 of the injection device. In this case, when the hold detent mechanism 230 is activated, the user hold force reduces by an amount substantially equal to the hold detent force. This reduces the required user hold force required to maintain the needle shroud 204 in a hold position. This provides the advantage that the user exerts less effort to maintain the needle shroud 204 in the hold position while waiting for the required dosage of medicament from the reservoir to be delivered via needle to the subject.

When the medicament is delivered, the user may release the applied reduced user hold force in which the control spring force of the control spring overcomes the hold detent force caused by pushing or sliding the second hold detent feature 230B in the distal longitudinal direction over the ramped surface 232 and planar surface of the thick portion 208b of the flexible arm 208a. This may further flex or bias the flexible arm 208a such that the thick portion 208b of the flexible arm 208a engages with the ramped recess 236 of the rear casing sheaf 206a, which further allows the second hold detent feature 230B of the needle shroud 204 to pass the thickened portion 208b of the flexible arm 208a of the collar 208 as the needle shroud 204 travel towards the final position or a locked position. The hold detent mechanism 230 is deactivated when it moves into a locking configuration for locking the needle shroud 204 in the final or locking position (e.g., similar to the initial position of the needle shroud 204) after the second hold detent feature 230B clears the distal end of the flexible arm 208a.

Once the second hold detent feature 230B of the needle shroud 204 clears the distal end of the flexible arm 208a the biassing force of the flexible arm 208a is released and the second hold detent feature 230B including the flexible arm 208a and thick portion 208b straightens such that it is substantially parallel to the longitudinal axis 231, which deactivates the hold detent mechanism 230. That is, the thick portion 208b is disengaged from the recess 236 and moves back to its original position as illustrated in FIG. 2B. Thus, the first and second hold detent features 202A and 202B of the hold dent mechanism 232 deactivate and the hold detent force 220 is released. In this example, the distal end of the flexible arm 208a (i.e., the distal end of the thick portion 208b) is square or rectangular shaped block and creates a non-return surface or lock that prevents the second hold detent feature 230B of the needle shroud 204 from moving longitudinally along the longitudinal axis 231 in the proximal direction. As well, the second hold detent feature 230B may engage with locking space 239 formed between the distal end of the thick portion 208b of the flexible arm 208a and the distal end of the collar 208. The position of the locking space 239 and/or the length of the thickened portion 208b of the flexible arm 208a of the first hold detent feature 230A of the collar 208 are configured such that, when locked, the needle shroud 204 is in a final position or locked position (e.g., similar to the initial position) in which the needle shroud 204 extends from the outer casing 202 and encloses the needle of the injection device. When locked, the needle shroud 204 is prevented from retracting and exposing the needle of the injection device.

FIGS. 2C-2F shows another example of a hold detent mechanism 240 in various stages of operation from the hold position of the needle shroud 204 to the final position or locking position of the needle shroud 204. For simplicity, reference numerals from FIGS. 2A and 2B are reused for similar or the same components or features. The needle shroud 204 and injection device body or outer casing 204 and rear casing 206 correspond to the needle shroud 118 and outer casing 102 and rear casing 114 of FIG. 1, respectively, but which are further modified to include hold detent mechanism 240.

Figure 2C:
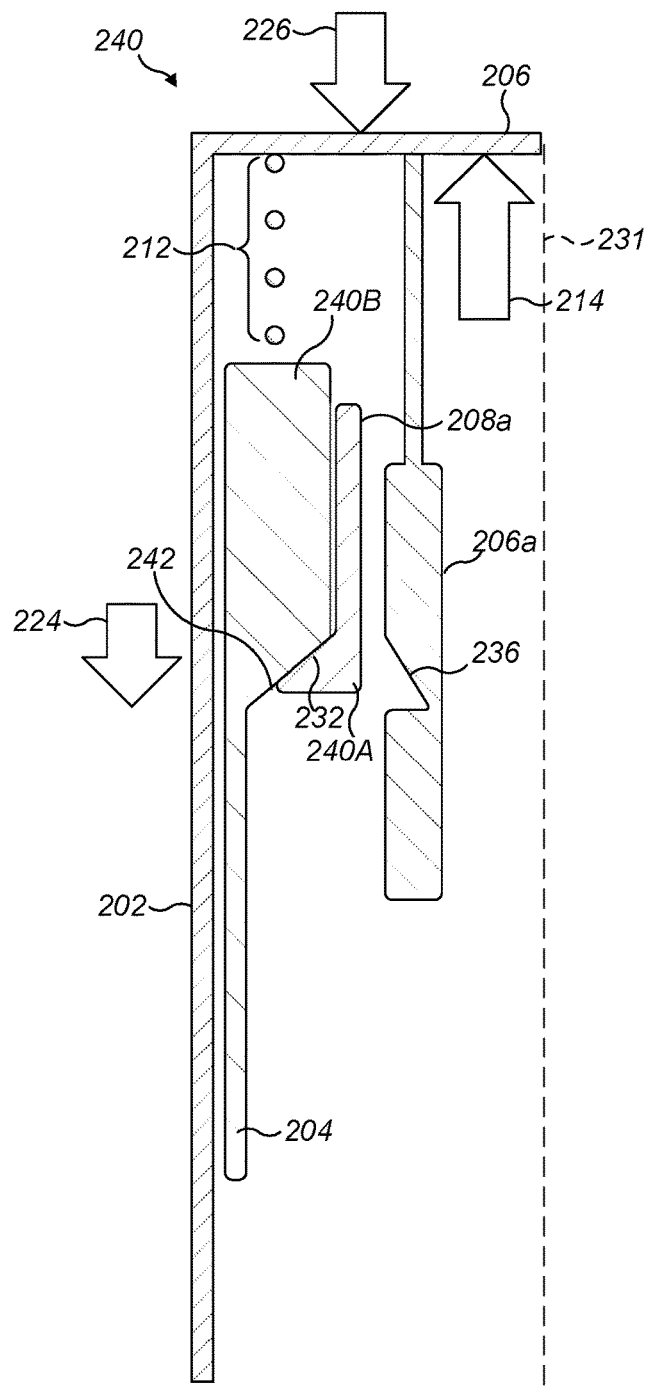
FIG. 2C shows a schematic example of a cross section of another hold detent mechanism for the injection device of FIG. 2A activated and in a hold position.

FIG. 2C shows an example cross-section schematic of a hold detent mechanism 240 of an injection device that includes first and second hold detent features 240A and 240B when activated in the hold position. In this example, the first hold detent feature 240A is coupled to a flexible arm 208a of the collar 208 and comprises a non-flexible male component with a ramped surface 232 at a distal end of the flexible arm. The flexible arm 208a forms part of the collar 208 (e.g., a snap fit or integral cut-out). The second hold detent feature 240B (e.g., a shroud pin) includes a non-flexible ramped male component with a ramped surface 242 with a gradient substantially opposite the gradient of the ramped surface 232 of the flexible arm 208 of the collar 208 such that when the hold detent mechanism 240 is activated in the hold position the ramped surfaces 232 and 242 meet in which at least a portion of the ramped surfaces 232 and 242 contact each other when engaged as depicted in FIG. 2C (e.g., the ramped surfaces 232 and 242 align and contact each other when engaged). The rear casing sheaf 206a also has a ramped indented surface or recess 236 that extends radially towards the longitudinal axis 231, and is configured to enable the flexible portion 208a of the collar 208 to be biased and flex the flexible arm 208a of the collar 208 such that, as illustrated in FIG. 2D, a distal end portion of the non-flexible ramped male component fills, at least in part, the ramped recess 236 so the second hold detent feature 230B can be guided in the distal direction and longitudinally over the ramped surface 232 of the first hold detent feature 230B as the needle shroud 204 moves away from the hold position and extend from the outer casing 202 to a final or locked position subsequent to the hold position as described with reference to FIGS. 2D to 2F.

In the hold position as shown in FIG. 2C, the user is applying a user hold force 226 along the longitudinal axis of the injection device in the distal direction to the rear casing 206 or outer casing 202, as the needle shroud 204 retracts to the hold position. When in the hold position, the hold detent mechanism 240 activates when the ramped surfaces 232 and 234 of the first and second hold detent features 240A and 240B engage with each other. The first and second hold detent features 240A and 240B engage each other when at least a substantial portion of the ramped surfaces 232 and 242 contact each other as depicted in FIG. 2C (e.g., the ramped surfaces 232 and 242 align and contact each other when engaged). The hold detent mechanism 240 is now activated. When the hold detent mechanism 240 is activated, the ramped surfaces 232 and 242 meet with and engage with each other creating a hold detent force 224 that is equal and opposite to a frictional force acting parallel to the longitudinal axis 231 which results from the force required to bias the flexible arm 208a (a resilient material) of the collar 208 radially towards the longitudinal axis 231 of the injection device. Thus, the user hold force 226 is reduced based, at least in part, on the additional hold detent force 224. In this case, when the hold detent mechanism 240 is activated, the initial user hold force reduces by an amount substantially equal to the hold detent force 224 resulting in the reduced user hold force 226. This provides the advantage that the user exerts less effort to maintain the needle shroud 204 in the hold position while waiting for the required dosage of medicament from the reservoir to be delivered via needle to the subject.

Figure 2D:
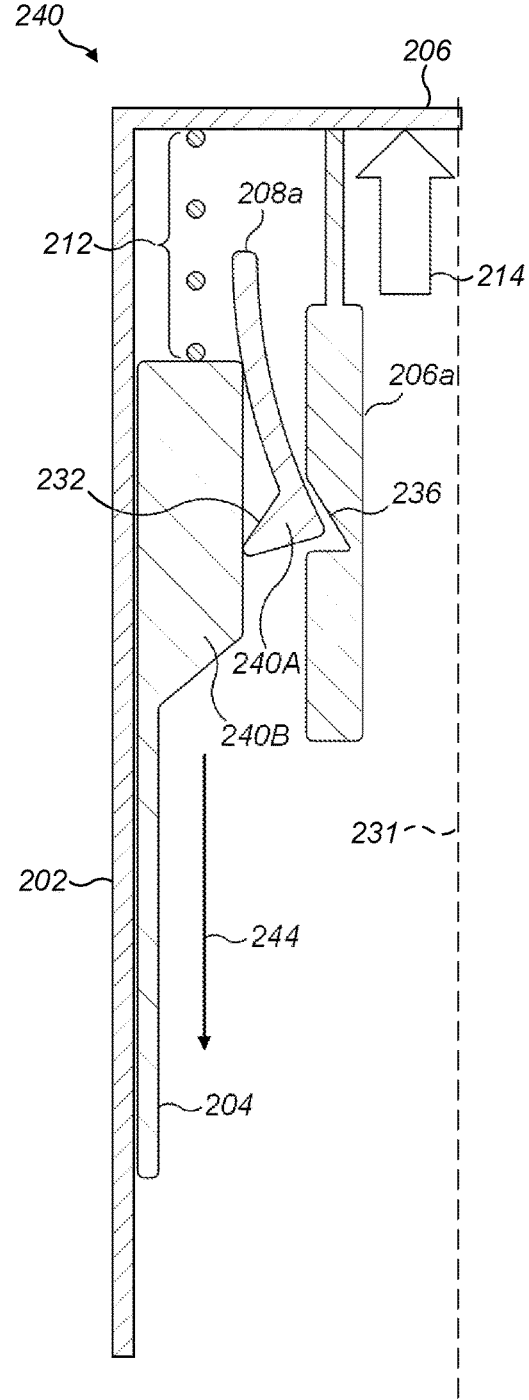
FIG. 2D shows a schematic example of a cross section of the hold detent mechanism of FIG. 2C deactivating and moving towards a final or locking position.
Figure 2E:
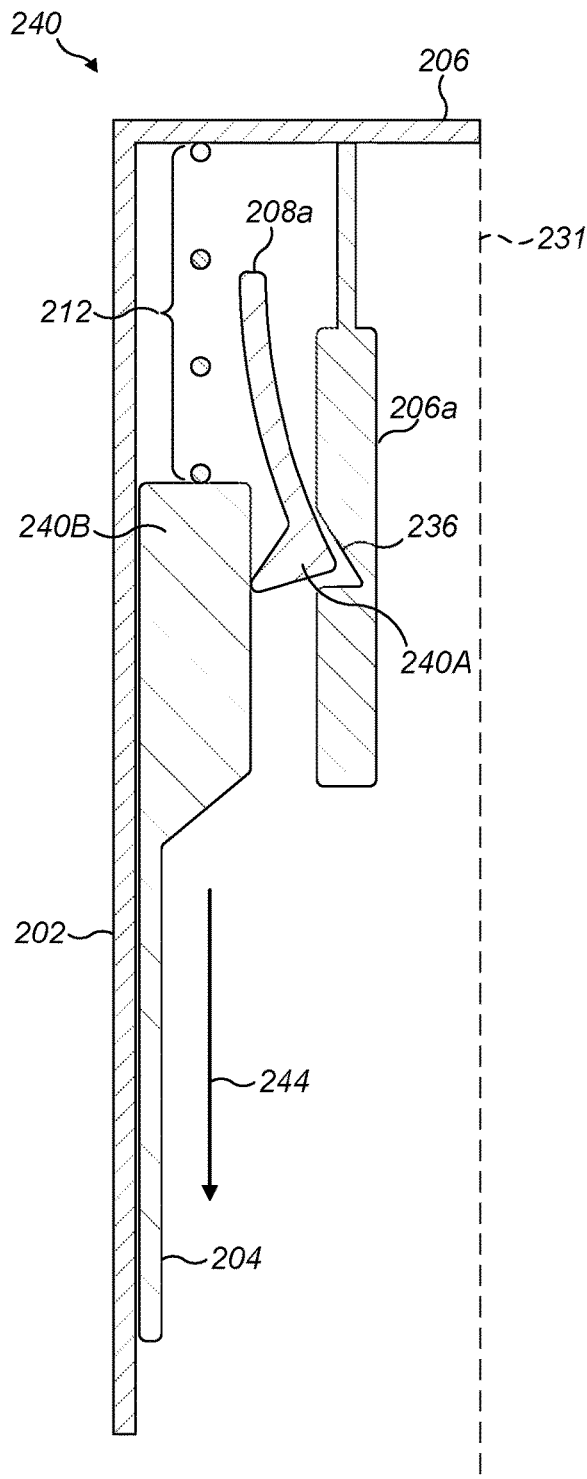
FIG. 2E shows a schematic example of a cross section of the hold detent mechanism of FIG. 2C deactivating and moving towards the final or locking position.

FIGS. 2D and 2E shows an example cross-section schematic of the hold detent mechanism 240 of the injection device of FIG. 2C when the medicament has been delivered and the user releases (e.g., relaxes) the applied reduced user hold force 226 in which the control spring force 214 of control spring 212 uncompresses and releases the control spring force 214, which overcomes the hold detent force 224 including the biassing force required to bias or flex the flexible arm 208a radially towards the longitudinal axis 231 of the injection device. The control spring force 214, when the hold detent force 224 is released, pushes or slides the second hold detent feature 240B of the needle shroud 204 in the distal direction 244 over the ramped surface 232. This further flexes or biases the flexible arm 208a such that a distal end portion of the non-flexible ramped male component of the flexible arm 208a engages with the ramped recess 236 of the rear casing sheaf 206a. This allows the second hold detent feature 240B of the needle shroud 204 to pass in the distal direction 244 over the non-flexible ramped male component of the flexible arm 208a of the collar 208. The control spring 212 causes the needle shroud 204 to extract from the outer casing 202 of the injection device towards a final or locked position. In FIGS. 2D and 2E the hold detent mechanism 240 is deactivating as the second hold detent feature 240B moves past the first hold detent feature 240A as the control spring force 214 causes the needle shroud 204 to extend and extract from the outer casing 202 of the injection device.

Figure 2F:
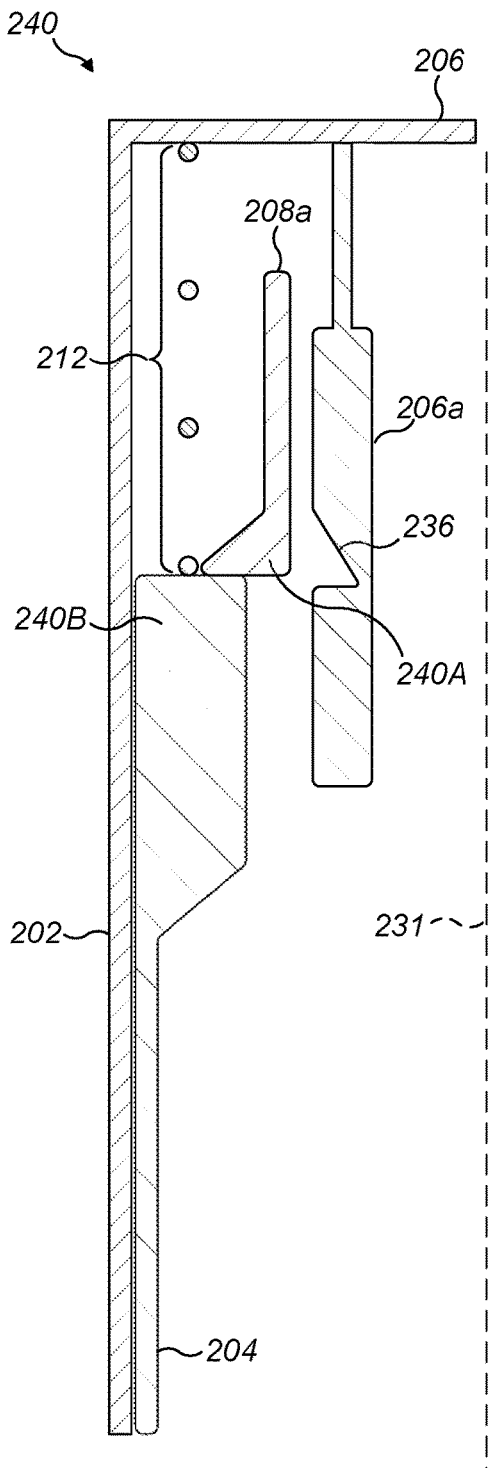
FIG. 2F shows a schematic example of a cross section of the hold detent mechanism of FIG. 2C deactivated and in the final or locking position.

FIG. 2F shows an example cross-section schematic of the hold detent mechanism 240 of the injection device of FIG. 2C when deactivated in which the needle shroud 204 has been extracted to a final position or locking position. The final position or locking position is when the needle shroud 204 encloses the needle of the injection device. FIG. 2F shows the needle shroud 204 and flexible arm 208a in a locking configuration, which locks the needle shroud 204 in the final or locking position (e.g., similar to the initial position of the needle shroud 204). In operation, once the second hold detent feature 240B of the needle shroud 204 clears the distal end of the non-flexible ramped male component of the flexible arm 208a the hold detent mechanism 240 deactivates in which the biassing force that is flexing the flexible arm 208a as shown in FIGS. 2D and 2E is released and the flexible arm 208a straightens (e.g., flexible arm 208a and ramped male component of the flexible arm 208a unflexes to lie in a plane that is substantially parallel to the longitudinal axis 231 of the injection device). Once the flexible arm 208a and ramped male component of the flexible arm 208a straighten and unflex, the non-flexible ramped male component of the flexible arm 208a is positioned to block or prevent the second hold detent feature 240B of the needle shroud 204 from retracting back into the outer casing 202 in a proximal direction towards the hold position as shown in FIG. 2C. If this is attempted, then the proximal end portion of the second hold detent feature 240B will contact the distal end portion of the ramped male component of the flexible arm 208a as illustrated in FIG. 2F such that the needle shroud 204 cannot be retracted any further, and so the needle shroud 204 is in a locked or final position. In the locked or final position, the surface of the distal end portion of the ramped male component of the flexible arm 208a is configured to block or prevent the second hold detent feature 240B from moving in the proximal direction back towards the hold position shown in FIG. 2C. The hold detent mechanism 240 has deactivated and the needle shroud 204 is locked or prevented from retracting back into the outer casing 202. In this example, the distal end of the non-flexible ramped male component of the flexible arm 208a is square or rectangular shaped and creates a non-return surface or lock that prevents the proximal end portion of the second hold detent feature 240B of the needle shroud 204 from moving longitudinally in the proximal direction. The position of the distal end of the non-flexible ramped male component of the first hold detent feature 240A and the proximal end of the second hold detent feature 240B are configured such that, when locked, the needle shroud 204 is in a final position or locked position (e.g., similar to the initial position) in which the needle shroud 204 extends from the outer casing 202 and encloses the needle of the injection device. When locked, the needle shroud 204 is prevented from retracting and exposing the needle of the injection device.

FIGS. 3A-3G shows an example of the operation of a collar 300 and needle shroud for use in injection device 100 or 200 with a hold detent mechanism as described with reference to FIGS. 2A-2F. The collar 300, hold detent mechanism and needle shroud corresponds to the collar 208, hold detent mechanism 210, 230 or 240 and needle shroud 204 of FIGS. 2A-2F.

Figure 3A:
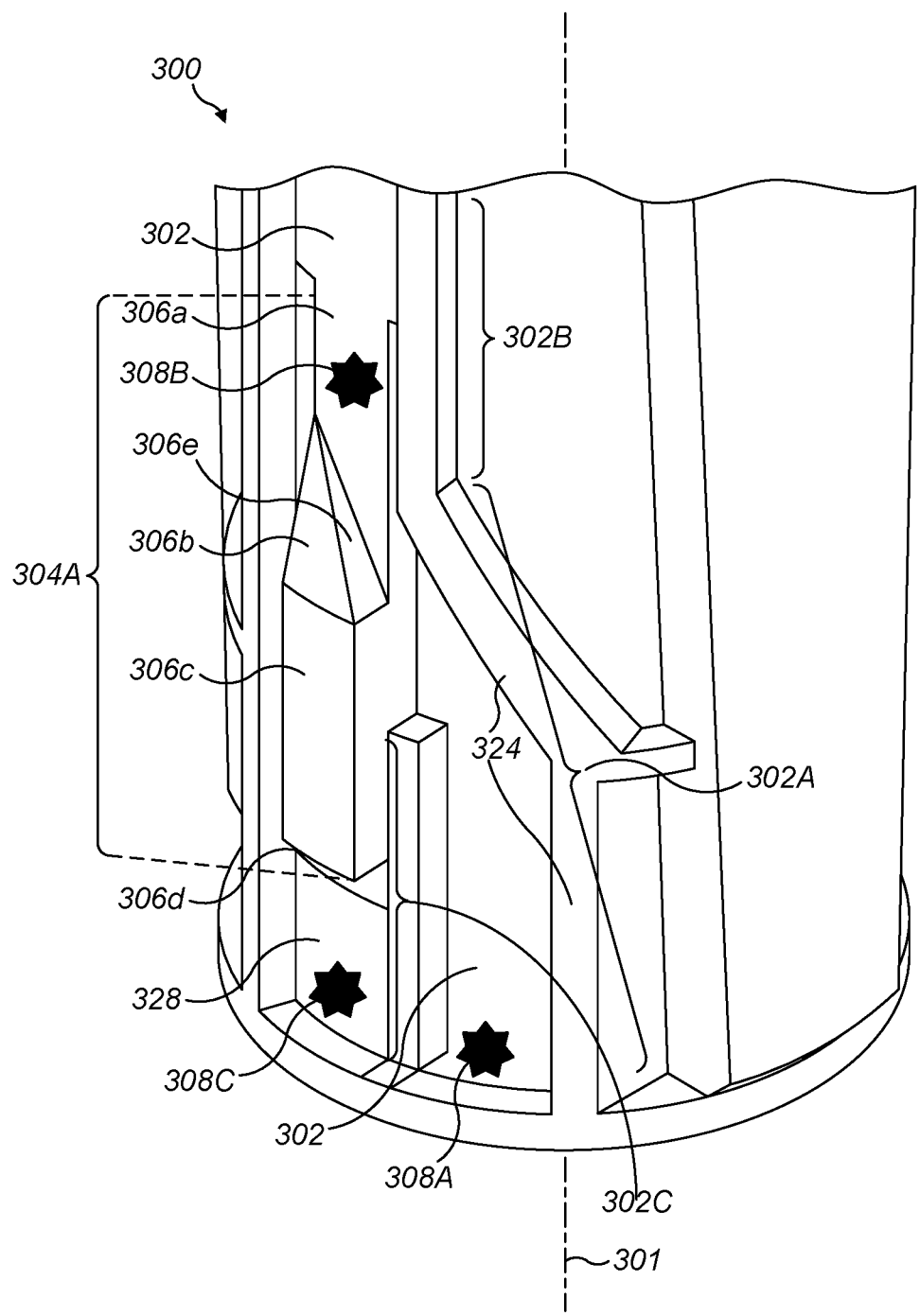
FIG. 3A shows a perspective schematic example of a collar for use with injection device of any of FIGS. 1-2F.

FIG. 3A shows a perspective schematic of an example collar 300 for use in the injection device as described herein with reference to FIGS. 1 to 2F. The collar 300 includes a cam track 302 on the surface thereof, where the cam track 302 includes a first portion 302A of the cam track 302 that extends and angles around the surface of the collar 300 and a second portion 302B of the cam 302 that intersects with the first portion 302A of the cam track 302 and extends parallel to the longitudinal axis 301 in the proximal direction of the collar 300. The second portion 302B of the cam track 302 includes, at least in part, a first hold detent feature 304A that includes a flexible arm 306a (or collar clip) that connects with an upper portion of second portion 302B of the cam track 302. The flexible arm 306a further includes a ramped surface 306b having a gradient that extends radially away from the surface of the cam track 302 of collar 300 and meets a planar surface block 306c of the flexible arm 306a with a planar surface that is parallel to the longitudinal axis 301 of the collar 300. As shown the first and second portions 302A and 302B of the cam track 302 also intersect with a third portion 302C of the cam track 302, where the third portion 302C of the cam track 302 is in line with the second portion 302B of the cam track 302 and extends in the distal direction parallel to the longitudinal axis 301 of the collar 300 or injection device. As shown, at least an end portion of the planar surface block 306c of the flexible arm 306a extends along the third portion 302C of the cam track 302. The planar surface block 306c of the flexible arm 306a ends in a rectangular or square shaped distal end 306d within the third portion 302C of the cam track 302. The rectangular or square shaped distal end 306d has an orthogonal surface to the planar surface of the planar surface block 306c. Adjacent to the base of the distal end 306d is a planar recess 328 in the collar 300 that lies at the base of the third portion 302C of the cam track 302. The ramped surface 306b of the flexible arm 306a intersects with a ramped wall 306e that forms part of the wall of cam track 302. The ramped surface 306b and ramped wall 306e are positioned in the vicinity of the intersection of the first portion 302A and second portion 302B of the cam track 302.

In addition, the black stars 308A, 308B and 308C illustrate the relative positions on the cam track 302 of the collar 300 for the second hold detent feature of the needle shroud when engaged with the cam track 302 that corresponds to when the needle shroud is in an initial position, hold position, and final or locked position, respectively. The cam track 302 is configured to engage with a second hold detent feature (not shown) of the needle shroud (not shown). The second hold detent feature (e.g., a shroud pin) of the needle shroud engages with the cam track 302 at the initial position 308A of the second hold detent feature. In this case, the initial position of the needle shroud also coincides with the position of the needle shroud with respect to the outer casing of the injection device, which extends from the outer casing of the injection device and encloses needle of the injection device. A control spring in the injection device is coupled to the needle shroud and biased to cause the needle shroud to be at least partially extended from the injection device body in the initial position 308A and so enclose the needle of the injection device. The collar 300 is rotatable within the injection device with respect to the injection device body or outer casing in which the cam track 302 is shaped to be engageable with the second hold detent feature of the needle shroud.

When the injection device is activated by the user, the needle shroud will retract into the outer casing of the injection device whilst the second hold detent feature of the needle shroud is guided by the walls 324 of the first portion 302A of the cam track 302 to travel via the cam track to the hold position 308B, the action of the second hold detent feature travelling via the first portion 308A of the cam track 302 rotates the collar 300 caused by the angular shape of the first portion 302A of cam track 302. The second hold detent feature travels along the first portion 302A of the cam track 302 causing the needle shroud to controllably retract into the outer casing of the injection device.

When the needle shroud is retracted from the initial position 308A on the cam track 302 into the injection device body to the hold position 308B on the second portion 302B of the cam track 302, the needle shroud has retracted into the outer casing of the injection device until the distal end of the needle shroud is substantially flush with the distal end of the outer casing of the injection device as illustrated with reference to FIG. 2A. This causes needle of the injection device to be exposed and enter the subject for delivering a dosage of a medicament to the subject. When the needle shroud has been retracted to its hold position, the second hold detent feature (not shown) of the needle shroud is positioned at hold position 308B on the second portion 302B of the cam track 302 of the collar 300. From this hold position 308B, the second hold detent feature is in a position such that it may be used by the user to activate the hold detent mechanism. Activation occurs when the second hold detent feature starts engaging with the ramped surface 306b of the first hold detent feature 304A to create the hold detent force for reducing the user hold force required to be maintained during delivery of the dosage of medicament to the subject. This may occur when the user relaxes the user hold force causing the second hold detent feature to engage with ramped surface 306b of the first hold detent feature 304A.

When initially in the hold position 308B, the second hold detent feature may only contact flexible arm 306a of the first hold detent feature 304A such that the hold detent force is not yet created for reducing the user hold force. The user hold force only starts to reduce when the hold detent mechanism is activated in the region of the hold position 308B. Activation of the hold detent mechanism occurs when the second hold detent feature (e.g., shroud pin (not shown)) starts to engage with and contact the ramped surface 306b of the first hold detent feature 304A to create the hold detent force. For example, when the user releases (e.g., relaxes slightly) a portion of the user hold force, this may enable the needle shroud and hence the second hold detent feature of the needle shroud to move in the distal direction parallel to the longitudinal axis 301 until the second hold detent feature starts to contact the ramped surface 306b of the flexible arm 306a of the first hold detent feature 304B. The created hold detent force reduces the user hold force as the second hold detent feature engages with the ramped surface 306b.

When the user of the injection device slightly reduces the user hold force (e.g., the user relaxes their hold slightly to activate the hold detent mechanism), this causes the control spring to extend needle shroud and the second hold detent feature (e.g., shroud pin) of the needle shroud towards the distal end of the device. This causes the second hold detent feature of the needle shroud to engage with the ramped surface 306b on the flexible arm 306a of the first hold detent feature 304A and/or thereafter the planar surface 306c on the flexible arm 306a of the first hold detent feature 304A. The geometry of contact surfaces of the first and second hold detent features 304A (e.g., contact surface of the shroud pin and contact surface of the ramped surfaces 306b and/or 306e) is such that it biases the shroud pin to move towards or in the direction of final or locked position 308C rather than initial position 308A. This engagement of the second hold detent feature (e.g., shroud pin) with the ramped surface 306b of the first hold detent feature 304A creates a hold detent force that is based on an opposite friction force acting parallel to the longitudinal axis 301 resulting from the engagement of the second hold detent feature with the ramped surface 304A and the force required to bias the flexible arm 306a (a resilient material) of the collar 300 such that the flexible arm 306a flexes radially towards the longitudinal axis 301 of the collar 208 or injection device. The hold detent force is opposite the control spring force caused by compression of the control spring during said retraction of needle shroud to said hold position 308B. The resulting hold detent force reduces the user hold force required to maintain the needle shroud in the region of the hold position 308B while the dosage of the medicament of the injection device is delivered via the needle to the subject. As well, the control spring can be designed and adjusted to apply a weaker control spring force than that required in prior art devices by such that the control spring force is still sufficient enough to, when compressed, power the needle shroud past the ramped and planar surfaces 306b and 306c of the flexible arm 306a (e.g., collar clip) and deactivate the hold detent mechanism. A weaker control spring force would also reduce the activation and hold forces necessary to operate the injection device.

After the medicament has been delivered to the subject, the hold detent mechanism is deactivated in which the second hold detent feature is disengaged from the ramped surface 306b of the first hold detent feature 304A by the user releasing or removing the user hold force (e.g., on injection device removal) and allowing the control spring force to overcome the hold detent force and cause the second hold detent feature to travel along the third portion 302C of the cam track 302 and over the ramped and planar surfaces 306b and 306c of the first hold detent feature 304A along the longitudinal axis 301 of the collar 300 to the final position or lock position 308C on the third portion 302C of the cam track 302. The geometry of contact surfaces of the first and second hold detent features 304A (e.g., contact surface of the shroud pin and contact surface of the ramped surfaces 306b and/or 306e) are configured such that it biases the shroud pin to move towards or in the direction along the third portion 302C of cam track 302 to the final or locked position 308C rather than initial position 308A on injection device removal. The travel of the second hold detent feature of the needle shroud towards the final or locked position 308C causes the distal end of the needle shroud to be extracted out of the outer casing of the injection device.

From the perspective of the second hold detent feature, the second hold detent feature is guided in the distal direction along the third portion 302C of cam track 302 from the region of the hold position 308B, where the second hold detent feature has been engaged with the ramped surface 306b, towards the final or lock position 308C located in a region at a distal end of the third portion 302C of the cam track 302. By disengaging the second hold detent feature from the first hold detent feature 304A, the hold detent force is released, which enables the control spring force of the control spring to extend the needle shroud from the injection device body to its final position in which the second hold detent feature of the needle shroud ends up in the final position 308C on the third portion 302C of the cam track 302 of the collar 308. In the final position 308C, the second hold detent feature of the needle shroud engages with the planar recess 328 in the collar 300, which is below the planar surface block 306c of the flexible arm 306a as the flexible arm 306a unflexes radially away from the longitudinal axis 301 as it straightens when the biassing force caused by engagement of the second hold detent feature to the ramped surface 306b of the first hold detent feature 304A is released. The planar surface block 306c of the unflexed or straightened flexible arm 306a forms a non-return surface configured to, subsequent to the extension of the needle shroud, lock the second hold detent feature of the needle shroud in the final position 308C and prevent further retraction of the needle shroud into the injection device body in the proximal direction along the third portion 302C of cam track 302 in a direction towards the hold position 308B.

FIGS. 3B-3G shows an example of the operation of the hold detent mechanism 310 of the collar 300 of FIG. 3A with needle shroud 312 for use in injection device 100 or 200 as described with reference to FIGS. 1 and 2A-2F. The collar 300, hold detent mechanism 310 and needle shroud 312 corresponds to the collar 208, hold detent mechanism 210, 230 or 240 and needle shroud 204 of FIGS. 2A-2F.

Figure 3B:
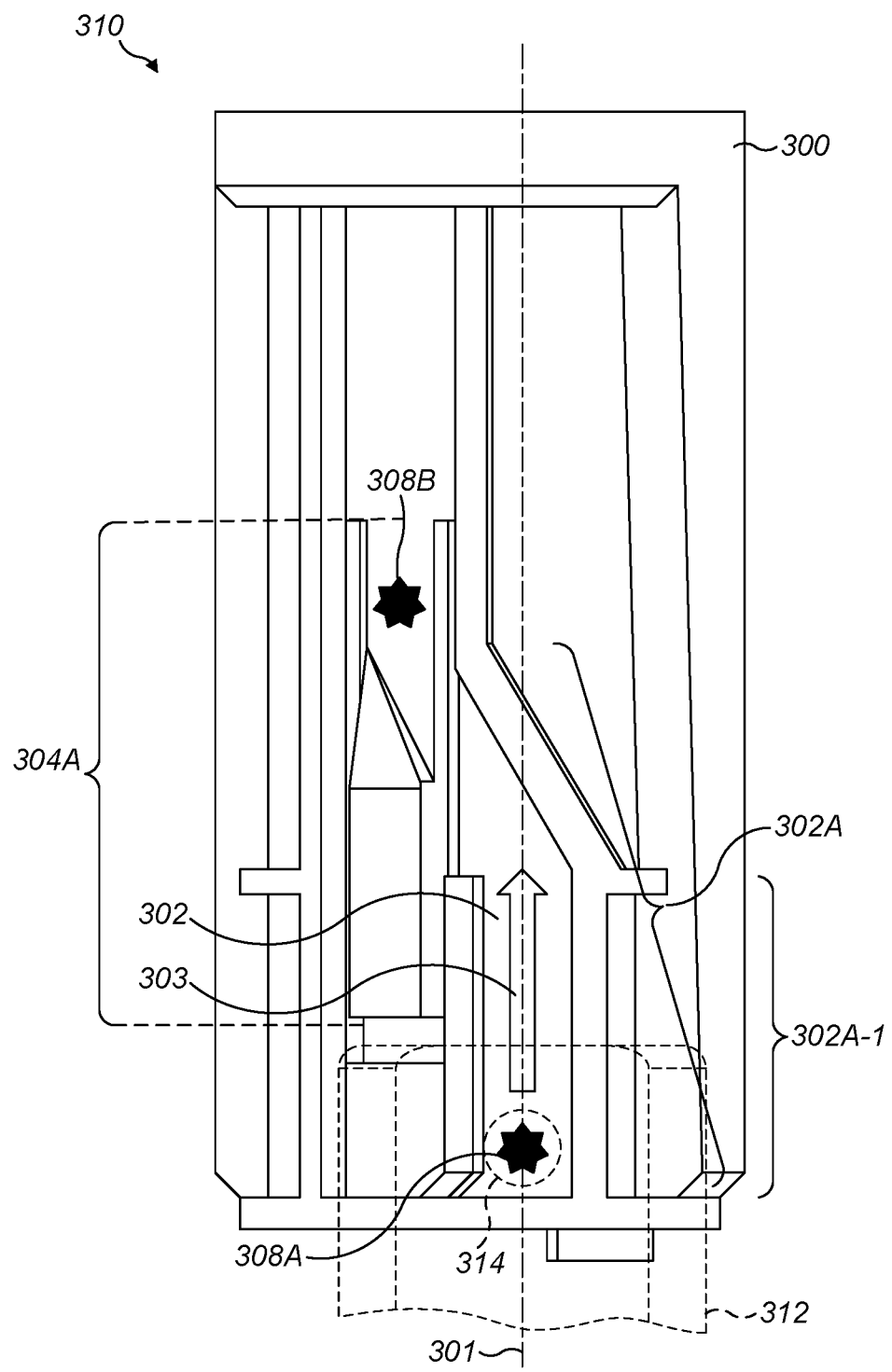
FIGS. 3B-3G shows a schematic example of the operation of collar of FIG. 3A.

FIG. 3B shows the initial position 308A of the second hold detent feature 314 (e.g., a shroud pin) of the needle shroud 312 prior to retraction of the needle shroud 312 into the injection device body, e.g., a pre-use position. In this stage, the needle shroud 312 will be extended from the outer casing of the injection device as illustrated in FIG. 1. In this example, the second hold detent feature 314 is in the form of a shroud pin 314 (represented by a dashed round circle). The shroud pin 314 of the needle shroud is configured to be engaged with first portion 302A of the cam track 302 of the collar 300 at the initial position 308A. The shroud pin 314 is also configured to be guided by the cam track 302 of the collar 300 from the initial position 308A towards the hold position 308B. When the shroud pin 314 is located at the initial position 308A of cam track 302, the distal end of the needle shroud 312 is in an extended position in which the distal end of the needle shroud 312 extends out of the outer casing of the injection device and covers the needle of the injection device. The shroud pin 314 of the needle shroud 312 is in the initial position 308A in the cam track 302 of the collar 300. The initial position 308A lies in the initial portion of the first portion 302A of the cam track 302. The shroud pin 314 is held in the initial position under a retaining force from the control spring (not shown). In this configuration the collar 300 may, in some examples, cause the plunger of the device (not shown) to be also retained in an initial position.

FIG. 3B illustrates the direction of motion that the shroud pin 314 of the needle shroud 312 takes along an initial section 302A-1 of the first portion 302A of the cam track 302 when the injection device is activated by the user. In this case, when the user presses the distal end of the needle shroud 312 onto an injection site of the subject, the user applies an activation force along the longitudinal axis 301 of the injection device that is strong enough to cause the control spring to compress and the needle shroud 312 to retract into the outer casing of the injection device. As the needle shroud 312 retracts, the shroud pin 314 of the needle shroud 312 is guided in a first axial longitudinal direction 303 by the initial section 302A-1 of the first portion 302A of the cam track 302 of collar 300 and starts to travel axially towards the proximal end of the injection device via the cam track 302 towards the hold position 308B.

Figure 3C:
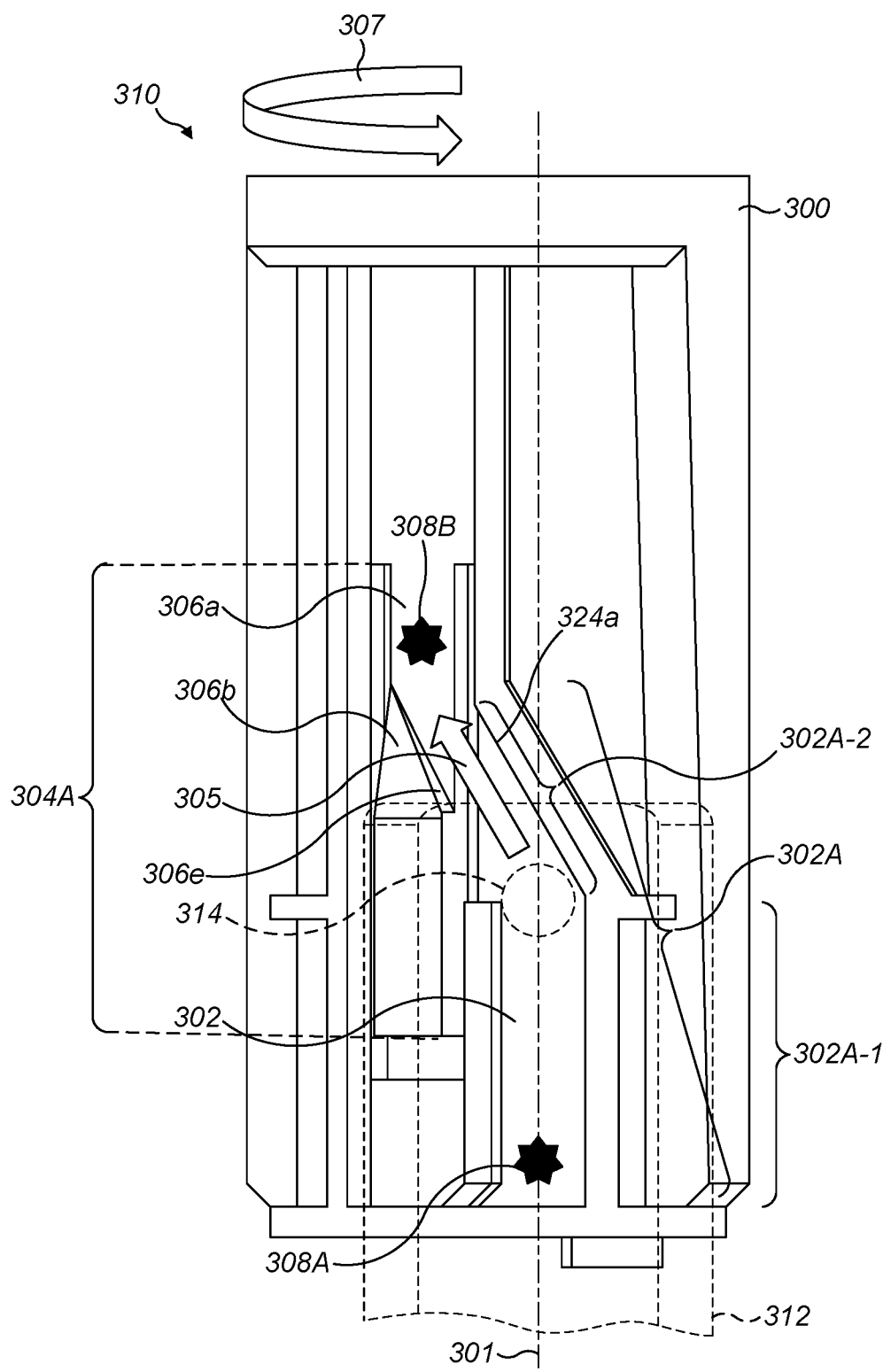

FIG. 3C shows an example of the needle shroud 304 retracting into the injection device body, e.g., during activation of the injection device when the user is pressing the distal end of the needle shroud 312 against the injection site of the subject. As the needle shroud 312 is retracted into the injection device body, FIG. 3C shows that the shroud pin 314 has moved along the initial section 302A-1 of the first portion 302A of the cam track 302 in the axial direction 303 until it reaches the first angled section 302A-2 of the first portion 302A of cam track 302. The upper walls 324a of this first angled section 302A-2 of the cam track 302 guides the shroud pin 314 in the second axial direction 305 towards the hold position 308B. Further retraction of the needle shroud 312 causes the shroud pin 314 to apply a force to the upper walls 324a of the first angled section 302A-2 of the cam track 302, which in turn causes the collar 300 to rotate in a rotational direction 307 about the longitudinal axis 301 of the injection device. The ramped wall 306e of the ramped surface 306b is shaped to form part of the lower wall of cam track 302 and positioned to prevent the shroud pin 314 from engaging with ramped surface 306b as the shroud pin 314 passes over the flexible arm 306a as it is guided towards the hold position 308A. That is, the ramped wall 306e forms a cut out in the ramped surface 306b that allows the shroud pin 314 to be guided past the ramped surface 306b in the vicinity of the intersection of the first portion 302A and second portion 302B of the cam track 302 without activating the first hold detent feature 304A. The shroud pin 314 causes the collar 300 to rotate until the shroud pin 314 reaches an upper end of the first angled section 302A-2 of the cam track 302, after which further retraction of the needle shroud 312 causes the shroud pin 314 to reach the hold position 308B.

Figure 3D:
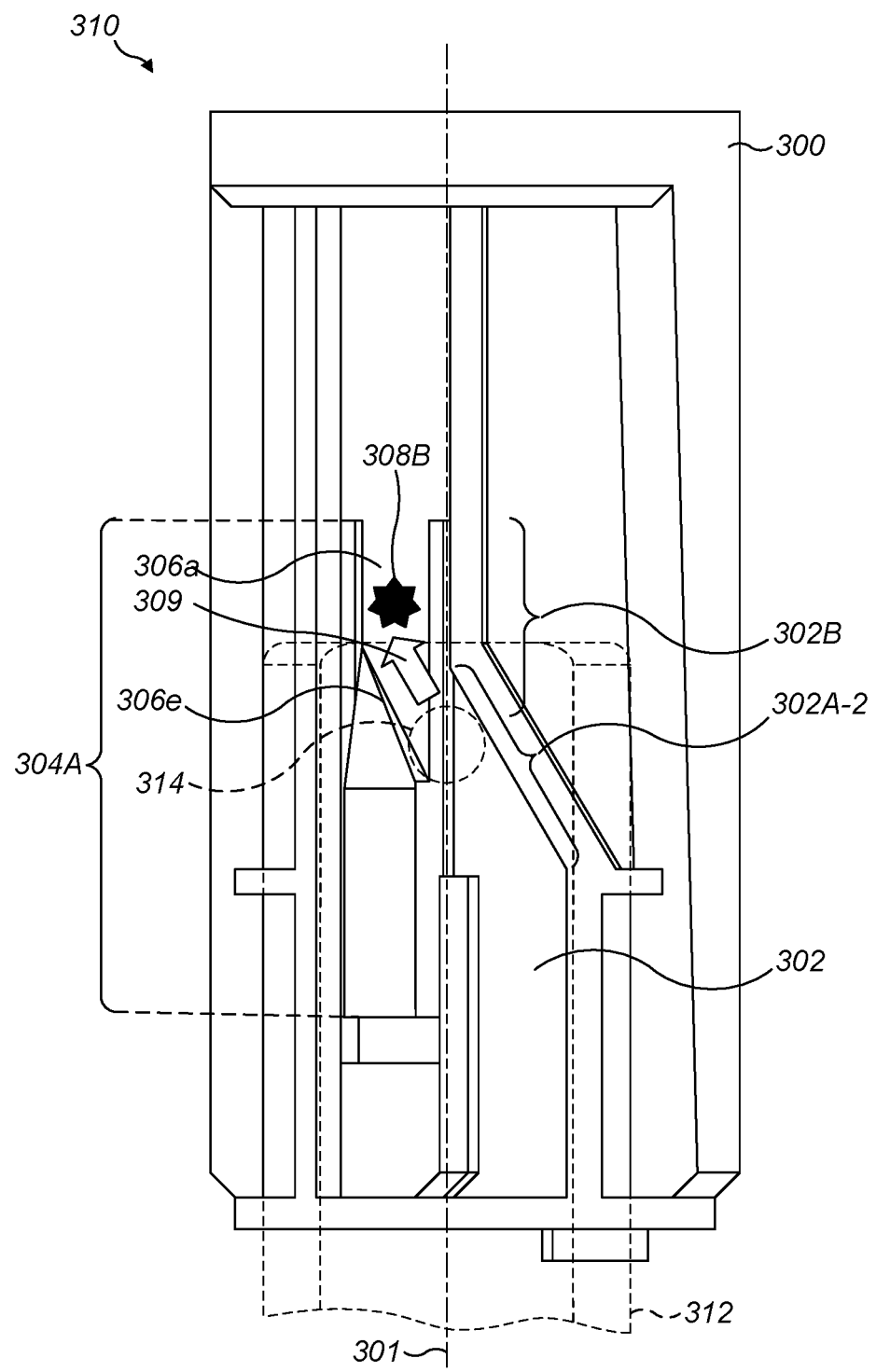

FIG. 3D shows an example of the shroud pin 314 in the vicinity or region of the intersection between the first angled section 302A-2 of the first portion 302A of cam track 302 and the second portion 302B of cam track 302. Further retraction of the needle shroud 312 causes the shroud pin 314 to follow the ramped walled surface 306e of the first hold detent feature 304A of the collar 300, which deflects the shroud pin 314 to move in a second axial longitudinal direction 309 towards the hold position 308B on the collar 300. The shroud pin 314 is shown moving between the ramped wall 306e which forms the lower wall of the cam track 302 through the cut out in the ramped surface 306b allowing the shroud pin 314 to be guided in the direction 309 past the ramped surface 306b without activating the first hold detent feature 304A (e.g., without engaging with the ramped surface 306b). This also causes the rotation of the collar 300 to end when the shroud pin 314 clears the ramped wall 306e. Depending on the tolerances, the needle shroud may further retract into the outer casing of the injection device to allow the shroud pin 314 to be guided in the second axial longitudinal direction 309 along second portion 302B of cam track 302 to the hold position 308B located on the flexible arm 306a prior to the intersection of the flexible arm 306a and ramped surface 306b.

Figure 3E:
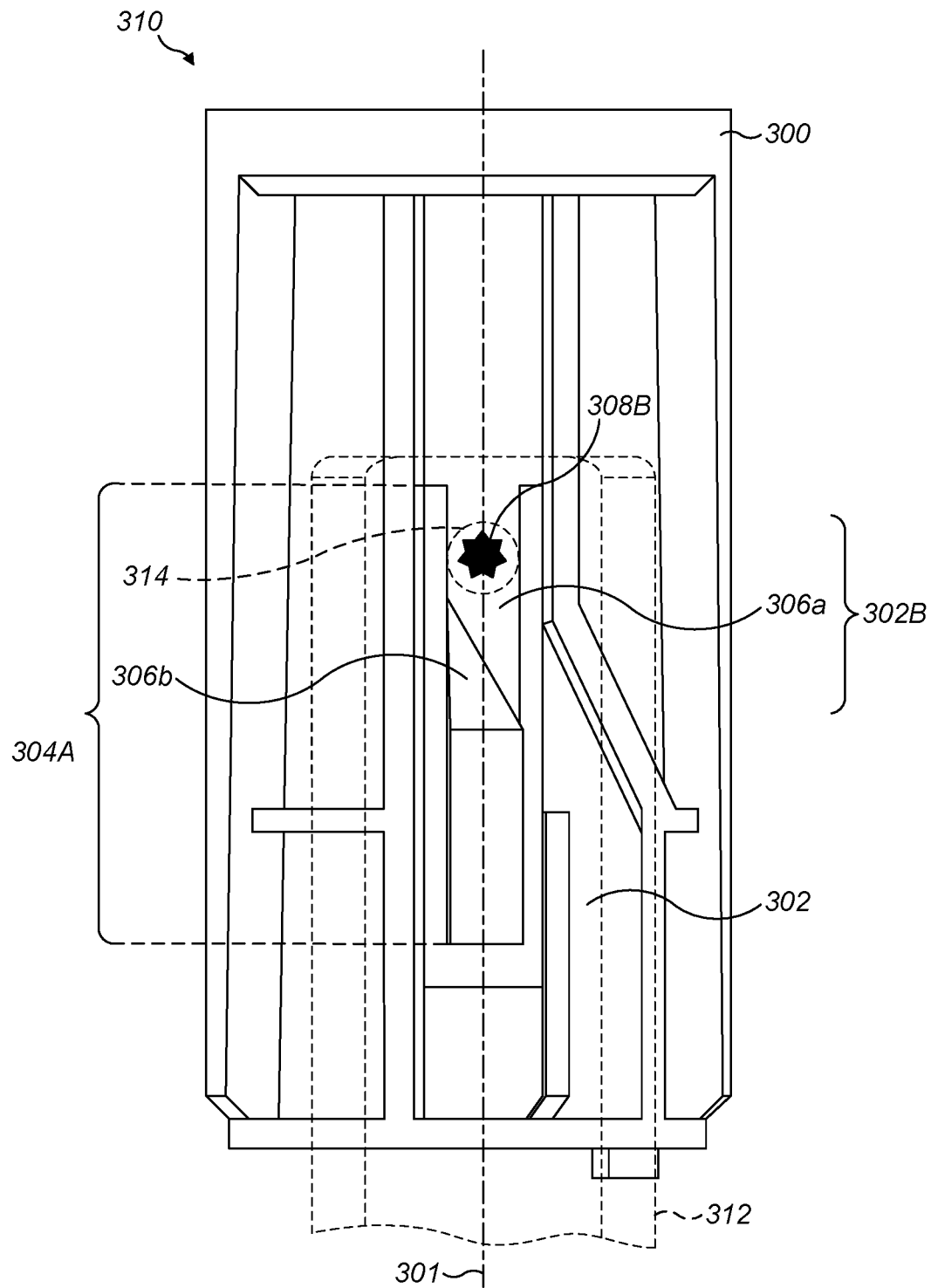
Figure 3F:
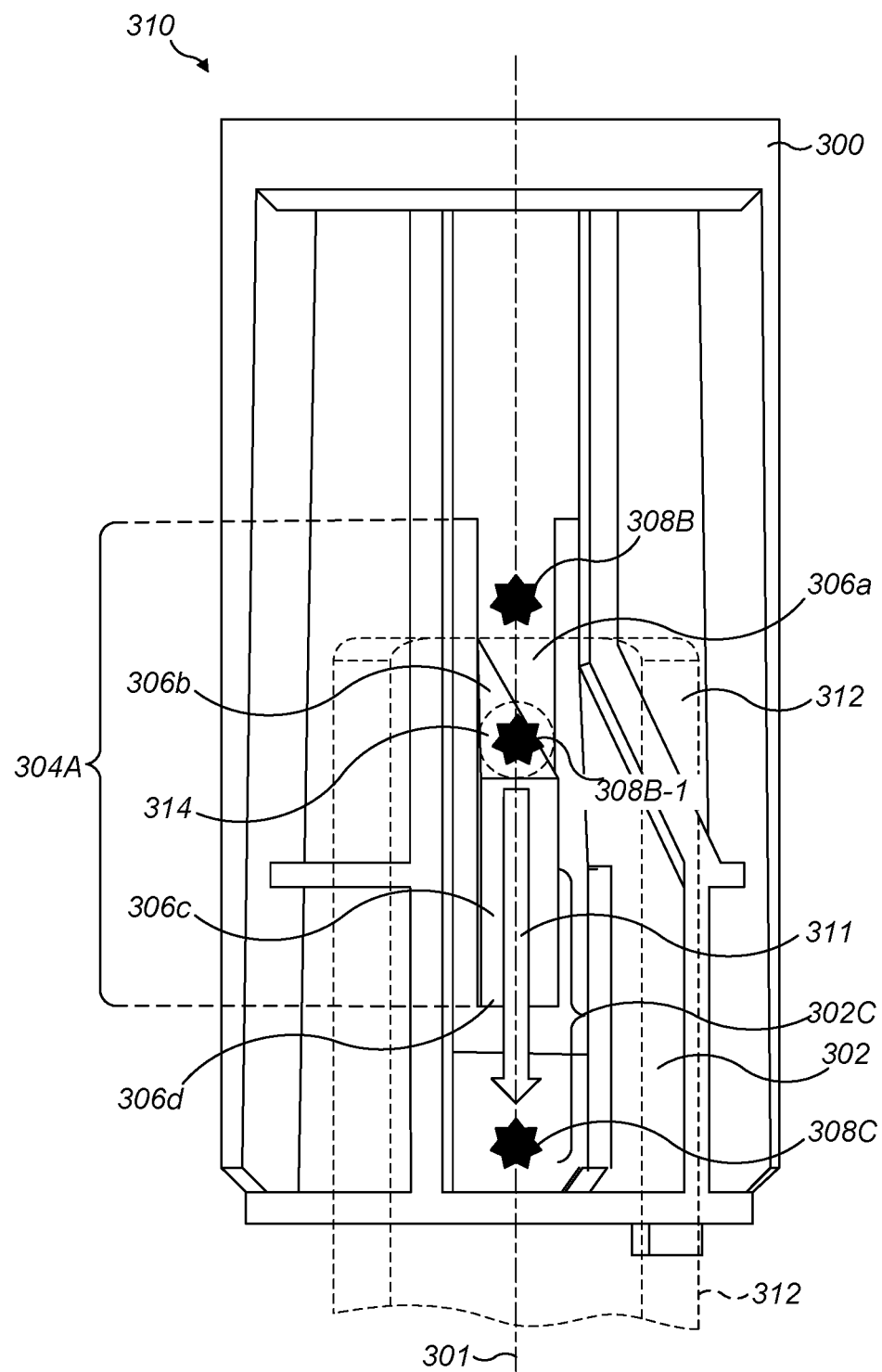

FIG. 3E shows an example of a hold configuration of the collar 300 in which the needle shroud 312 and the needle shroud pin 314 have reached the hold position 308B on the flexible arm 306a the vicinity of where the flexible arm 306a meets the first ramped surface 306b without the shroud pin 314 engaging with the ramped surface 306b of the first hold detent feature 304A. In this case, the hold detent mechanism has not yet activated because the shroud pin 314 has not yet engaged with the ramped surface 306b of the first hold detent mechanism 304A. In this configuration, the injection device may be configured to expel or deliver the medicament from the injection device via a needle, which has been exposed and has entered the injection site of the subject. The hold detent mechanism 310 is activated when the shroud pin 314 moves from the initial hold position 308B in a distal direction along the longitudinal axis 301 of the injection device or collar 300 to engage with the first ramped surface 306b of the first hold detent feature 304A as illustrated in FIG. 3F. This can be caused, as described with reference to FIG. 3A and FIGS. 2A-2F, by the user reducing the user hold force to cause the control spring to start a minimal extraction of the needle shroud and hence move the shroud pin 314 to engage with ramped surface 306b of the first hold detent mechanism 304A. The engagement of the shroud pin 314 with the ramped surface 306b creates the hold detent force that is opposite to the control spring force of the control spring and reduces the user hold force on the injection device whilst in the hold position 308B.

FIG. 3F shows an example of the hold detent mechanism 310 being activated when the shroud pin 314 engages with ramped surface 306b in an activated hold position 308B-1 creating a substantial hold detent force that is opposite the control spring force, which reduces the user hold force required to maintain the needle shroud in a hold position whilst the dosage of medicament is being delivered via needle of the injection device to the subject. The geometry of contact surfaces of the shroud pin 314 and ramped surfaces 306b and 306e are configured to bias the shroud pin 314 to move in the direction along the third cam portion 302C of cam track 302 towards the final or locked position 308C rather than in the direction along the second portion 302B of cam track 302 towards the initial position 308A. The hold detent mechanism 310 is activated when the shroud pin 314 has engaged and contacts the ramped surface 306b where the flexible arm 306a of the collar 300 meets the ramped surface 306b. FIG. 3F illustrates when the shroud pin 314 is fully engaging the ramped surface 306b in the activated hold position 308B-1 to create the hold detent force, which is equal and opposite to a friction force caused by the contact of the shroud pin 314 with ramped surface 306b in which the friction force acts parallel to the longitudinal axis 301 and results from the force required to bias the flexible arm 306a (a resilient material) of the collar 300 to cause the flexible arm 306a to flex radially towards the longitudinal axis 301 of the injection device. The hold detent force reduces the required user hold force during delivery of the medicament to the subject.

Once the correct dosage of medicament has been delivered to the subject, the hold detent mechanism 310 is deactivated by disengaging the shroud pin 314 from the ramped surface 306b and planar surface of the planar surface block 306c. This deactivating is achieved by the user releasing the user hold force (e.g., injection device removal) such that the control spring force overcomes the hold detent force to cause the shroud pin 314 to move and be guided along the third portion 302C of the cam track 302 from the activated hold position 308B-1 in a third axial longitudinal direction 311 along the third portion 302C of the cam track 300 that extends axially in a longitudinal direction towards a final or locking position 308C at the distal end of the collar 300. The geometry and design of the ramped surfaces 306b and 306e are configured to ensure that the needle shroud pin 314 moves in the third axial longitudinal direction 311 to end up in the final or locked position 308C after injection device removal rather than being pushed back towards the initial position 308A. Although FIGS. 3A to 3G illustrates a particular design and geometry of ramped surfaces 306b and 306e, this is by way of example only and the invention is not so limited, it is to be appreciated by the skilled person that any other suitable design or geometry of ramped surfaces 306b and 306e is applicable as long as the geometry of these ramped surfaces 306b and 306e ensures the shroud pin 314 to move, when injection device removed or user hold force released, in the third axial longitudinal direction 311 to end up in the final or locked position 308C. As the shroud pin 314 moves in the longitudinal direction 311 the needle shroud 312 extends out of the injection device body causing the needle to be removed from the body of the subject.

In this case, the user of the injection device releases the user hold force to the extent that the control spring force overcomes the hold detent force that is causing the flexible arm 306a to be radially flexed towards the longitudinal axis 301 of the injection device and moves the shroud pin 314 along the third portion 302C of the cam track 302 in the third axial longitudinal direction 311 to clear the ramped surface 306b and planar surface block 306c of the flexible arm 306a. The compression of the control spring during said retraction of needle shroud and shroud pin 314 to said hold position 308B creates the control spring force that, when released, powers the shroud pin 314 of the needle shroud 312 past the ramp surface 306b of the flexible arm 306a and the planar surface block 302c thus overcoming the hold detent force. However, given the hold detent mechanism 310, the control spring can be configured to apply just enough force that, when compressed, has the minimal necessary spring force to power the shroud pin 314 of the needle shroud 312 past the planar surface block 306c of the flexible arm 306a (e.g., collar clip) such that the shroud pin 314 clears the distal end 306d of the planar surface block 306c to thereby deactivate the hold detent mechanism. It has been found that the control spring force necessary to do this can be weaker than the control spring force of prior art injection devices, which further reduces the activation and hold forces necessary to operate the injection device.

In FIG. 3F, the shroud pin 314 travels over the ramp surface 306b of the flexible arm 306a of the first hold detent feature 304A of the collar 300 causing the flexible arm 306a to radially flex towards the longitudinal axis 301 of the injection device. As the needle shroud 312 extends out of the injection device, for example under the force of the control spring, the shroud pin 314 moves along the third axial longitudinal direction 311 along the third portion 302C of cam track 302. In doing so, the shroud pin 314 will also pass over the planar surface of the planar surface block 306c of the flexible arm 306a towards the final or locking position 308C.

As the needle shroud 312 continues to extend the shroud pin 314 clears or moves past the distal end 306d of the planar surface block 306c of the flexible arm 306a (i.e., the distal end of the flexible arm 306a) of the first hold detent feature 304A, which causes the flexible arm 306a to release the force that is biasing the flexible arm radially towards the longitudinal axis 301 of the injection device caused by the friction force created by the shroud pin 314 engaging and travelling over the first ramp surface 306b and planar surface of the planar surface block 306c of the flexible arm 306a. The shroud pin 314 clearing the distal end 306d of the planar surface block 306c causes the hold detent mechanism 310 to deactivate. Once the force biasing the flexible arm 306a is released, the flexible arm 306a radially flexes towards the outer casing of the injection device to straighten such that the flexible arm 306a and planar surface block 306c move to their initial positions in which they are aligned substantially parallel to the longitudinal axis 301. Thus, by the time the shroud pin 314 arrives at the final or locking position 308C, the flexible arm 306a has straightened in which the distal end 306d of the planar surface block 306d of the flexible arm 306a is configured create a non-returnable surface or shape (e.g., a rectangular block) that creates a "blockage" in the third portion 302C of cam track 302 for preventing travel of the shroud pin 314 in an opposite direction to the third axial longitudinal direction 311, i.e., back towards the hold position 308B. This prevents the shroud pin 314 from returning along the third portion 302C of the cam track 302 towards the activated hold position 308B-1 or hold position 308B. The shroud pin 314 may also be shaped such that it cannot travel over the distal end 306d of the planar surface block 306d of the flexible arm 306a in an opposite direction to the third axial longitudinal direction 311, i.e., back towards the hold position 308B.

Figure 3G:
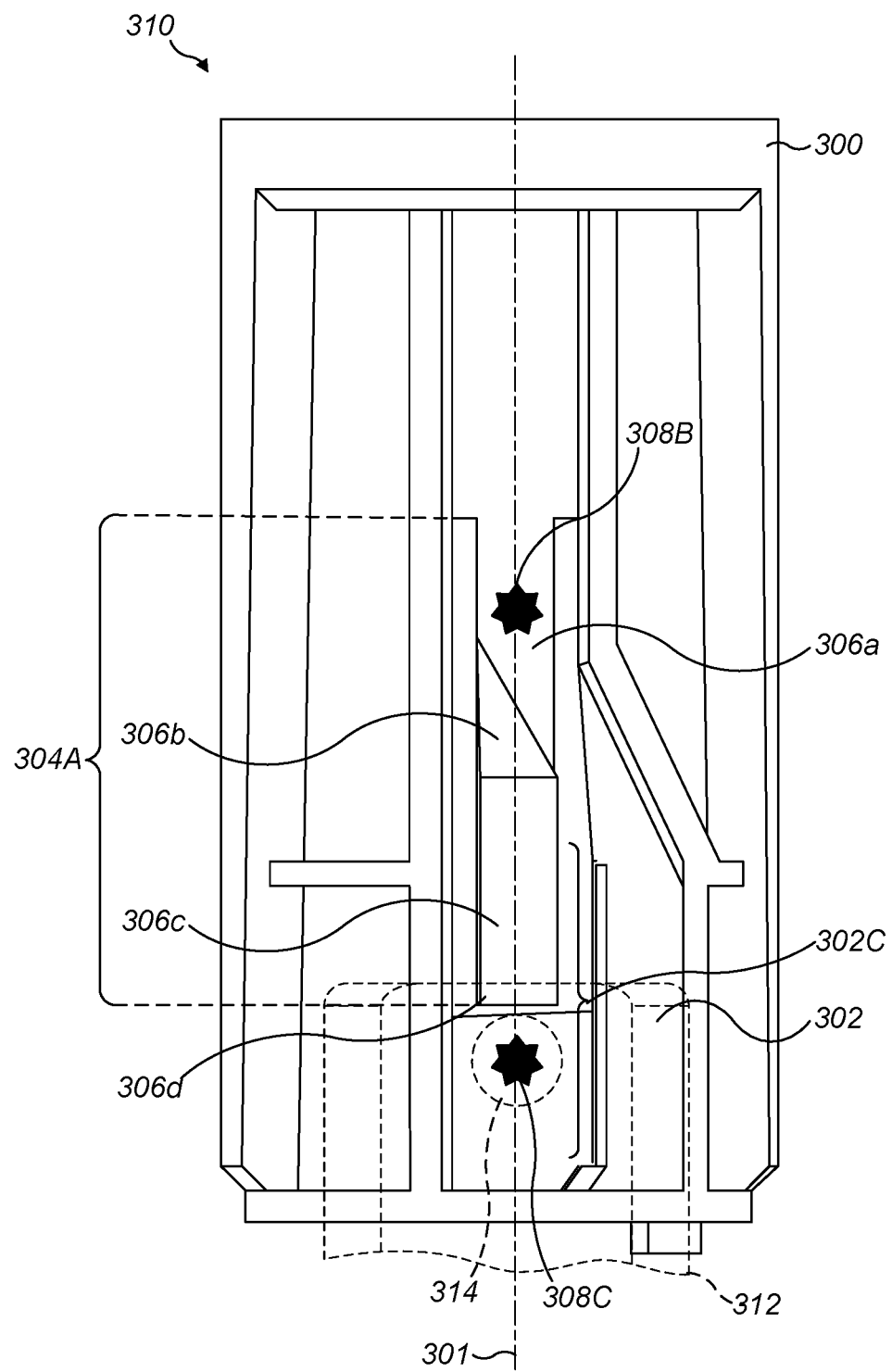

FIG. 3G shows an example of a locked configuration of the collar 300, the needle shroud 312 and shroud pin 314 after the needle shroud 312 has extended from the outer casing of the injection device body after hold detent mechanism 310 has been deactivated. In this configuration, the shroud pin 314 is locked in a final position 308C of the cam track 302. The non-return surface created by the distal end 306d of the planar surface block 306c of the flexible arm 306a blocks the proximal movement of the shroud pin 314 in the longitudinal direction towards the hold position 308B and so prevents further retraction of the needle shroud 312 into the injection device (and thus expose of the needle). The non-return surface that is created traps the shroud pin 314 when it moves in the longitudinal axial direction towards the proximal end of the injection device.

The distal end 306d of the planar surface block 306c of the flexible arm 306a may be shaped to create a non-return surface, which may, for example, comprise an angled surface, wall or rectangular block shape that is arranged to prevent the shroud pin 314 from travelling over the distal end 306d and the planar surface block 306c towards the hold position 308B. For example, the angled surface, and size of the wall or rectangular block shape of the distal end 306d is configured to prevent movement of the shroud pin 314 in the direction towards the hold position 308B when the shroud pin 314 is pushed against the distal end 306d of the planar surface block 306c during any further attempts to retract the needle shroud 312 after use.

Figure 4:
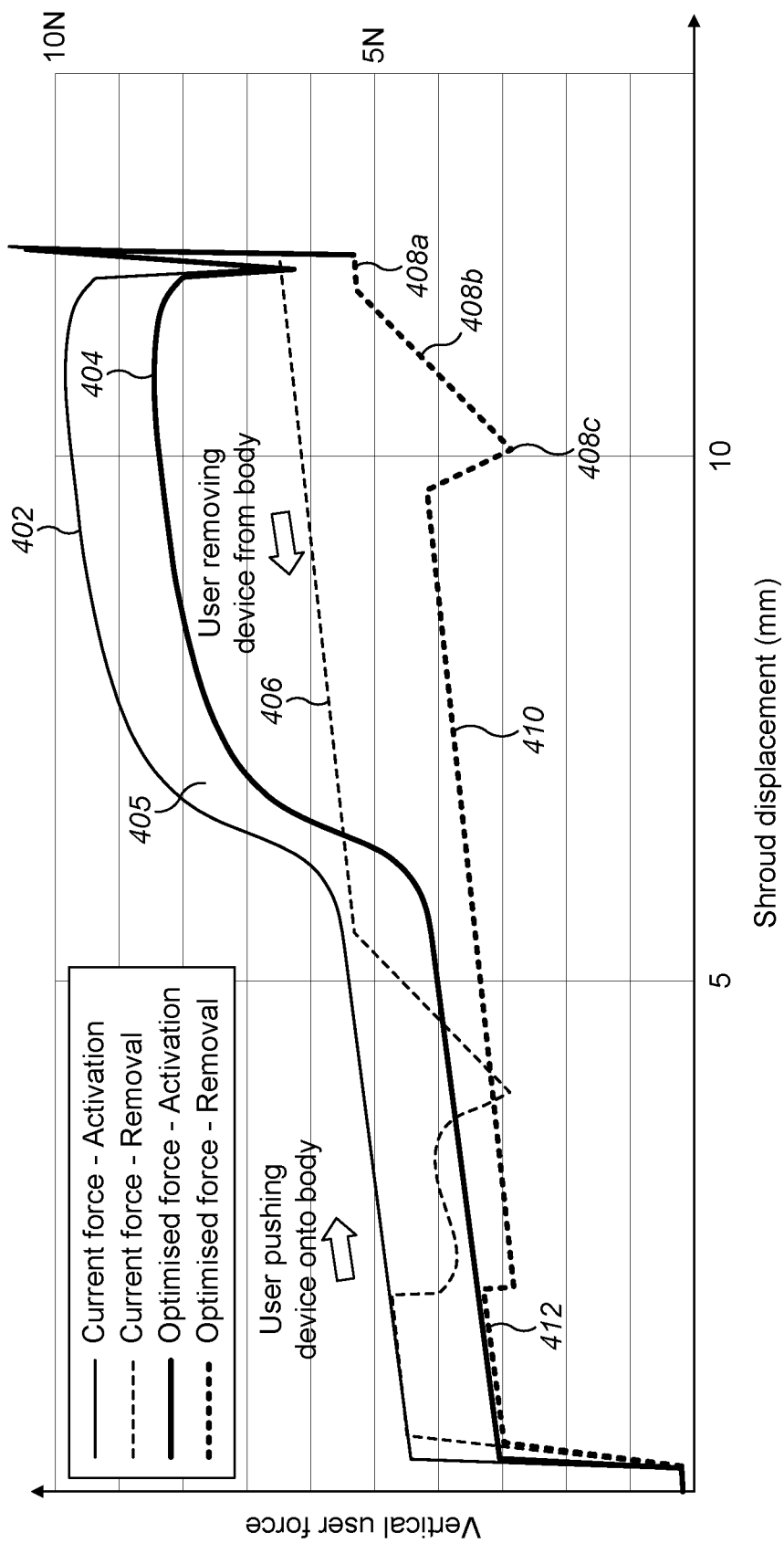
FIG. 4 shows an example comparison of force profiles of an injection device during use.

FIG. 4 shows an example comparison of force profiles of an injection device during use. The graph shows a magnitude of a vertical force applied (in Newtons, N) by a user as a function of needle shroud displacement (in mm) during insertion and removal of the device from a patient's body for both a prior art injection device (e.g., using a prior art needle locking mechanism) and a device using a collar as described herein.

The first trace 402 shows the force profile of the activation force of a prior art device without a hold detent mechanism as described herein when a user is pushing the device onto an injection site of a subject's body. The second trace 404 shows the force profile of the activation force of an injection device according to embodiments of the present invention as described with reference to any of FIGS. 2A to 3G when the user is pushing the device onto the injection site of a subject's body. The third trace 406 shows the force profile of a prior art device when a user is removing the device from the injection site of the subject's body. The fourth trace depicted by trace sections 408a-408c, 410 and 412 shows the force profile of an injection device according to embodiments of the present invention as described with reference to any of FIGS. 2A to 3G when the user is removing the device from the injection site of subject's body.

As can be seen, comparison 405 between the force profiles of the first and second traces 402 and 404 illustrates the differences in these force profiles in which the force profile of the second trace 404 has substantially decreased meaning the user requires less activation force for retracting the needle shroud of the injection device. This is because the advantage of the hold detent mechanism in the collar as described with reference to FIGS. 2A to 3G means that a weaker control spring may be used than used in prior art devices whilst still enabling activation and deactivation of the hold detent mechanism of the collar according to embodiments of the invention. The reduction in activation force is approximately 1 to 2N of force. This means the user may apply less activation force to the injection device, and less user hold force whilst maintaining the injection device in the hold position, which is further reduced due to the hold detent force due to activation of the hold detent mechanism when injection device is in the hold position.

However, more importantly, the fourth trace depicted by trace sections 408a-408c, 410 and 412 shows a significant reduction in the hold force required by the user when the hold detent mechanism 310 of the collar 300 is activated in the hold position as described with reference to FIGS. 3A to 3G. Trace sections 408a-408c illustrate the hold force required to hold the injection device in the hold position. Trace section 408a is due to the reduction in user hold force required to allow the second hold detent feature to travel and engage with the first hold detent feature of the hold detent mechanism to activate the hold detent mechanism (e.g., when shroud pin 314 moves to engage with the ramped surface 306b of FIG. 3E). Trace 408b illustrates the increase in hold detent force as the second hold detent feature further engages the first hold detent feature (e.g., as the shroud pin 314 further engages the ramped surface 306b of FIG. 3F), which is represented as a decrease in user hold force to a minimum user hold force of approximately 3N when the second hold detent feature is engaged with the first hold detent feature to provide a maximal hold detent force. This reduced user hold force of 3N may be maintained during delivery of the medicament to the body of the subject. This reduction in hold force by the user improves the ability of the user to ensure the correct dosage of the medicament to be delivered whilst minimising discomfort and/or pain to the subject. The hold detent mechanism reduces the force that a user has to apply to maintain the needle shroud of the injection device 300 in the hold position by approximately 3 N at the peak hold detent force (see trace section 408c), which is helping to further reduce the user hold force compared with the prior art device (e.g., compare see traces 406 and 408c). The prior art injection device requires approximately double the required user hold force at the peak hold detent force, or minimal user hold force.

On device removal, the removal force profile 410 for the device utilising embodiments described herein and with the addition of a weaker control spring that is just strong enough to overcome the hold detent force and/or the biassing force of the flexible arm or clip of the collar and automatically extend the needle shroud to the final or locking position also differs from the prior art device removal profile 406 in that there is essentially a constant reduction in force required by the user in the range of approximately 2 N. This reduction in force is caused by the weaker control spring force and additional friction of the flexible arm (e.g., collar clip) on the needle shroud of the injection device that is supporting part of the control spring force. This reduction in remove force further improves user control of the device during removal and reduces or minimises discomfort and/or pain to the subject. The force profile of trace section 412 is slightly elevated because as the needle shroud clears the flexible arm of the collar (e.g., collar clip) as described with reference to FIGS. 3A to 3G, the full control spring force without friction between collar and needle shroud is experienced again. This enables the needle shroud to be fully extended to enclose the needle of the injection device whilst also ensuring the needle shroud is automatically locked in the final position or locking position by the non-return surface of the flexible arm or collar clip to prevent the needle shroud from retracting to expose the used needle of the injection device.

Although the hold detent mechanisms and first hold detent feature are described herein as being a flexible arm or clip, this is by way of example only and the invention is not so limited, it is to be appreciated by the skilled person that modifications may be made to the hold detent mechanism and/or first hold detent feature (and/or the second hold detent feature) such that they are suitable for activating the hold dent mechanism for creating a hold force when the needle shroud is at the hold position and deactivated when the medicament is delivered and needle shroud extends to substantially the final or locked position in which part of the needle shroud extends out of the outer casing of the injection device and encloses the used needle. A locking mechanism, e.g., non-return surface etc., may be used to ensure the needle shroud is prevented from retracting and exposing the used needle of the used injection device. In some embodiments or modifications, the resilient and/or flexible arm or clip of the hold detent mechanism and/or the first hold detent feature may include, without limitation, for example a resilient/flexible partial cut-out or resilient "flap" on the collar with a corresponding second hold detent feature for engaging or interacting with the partial cut-out or flap (e.g., the second hold detent feature may be a shroud pin or male component that engages with a ramped surface on the partial cut-out or resilient flap to create the hold force as described herein). In other embodiments or modifications, the resilient and/or flexible arm or clip of the first hold detent feature may be a spring loaded flap or arm that snap-fits to the collar, where the spring loaded flap is biased by a spring for engaging with a second hold detent feature (e.g., shroud pin or male component) to create the hold detent force, which may be overcome by the control spring force when the user releases the user hold force.

Alternatively or additionally, rather than flexible arms or clips, further modification to the hold detent mechanism may include configuring the first and second hold detent features to be resistive features that activate when the needle shroud is in the hold position such that the first and second hold detent features engage to create a resistive force that creates a hold detent force for reducing the user hold force and counteracting the control spring force in the hold position, and when the user releases the hold force the resistive features are configured to release the hold dent force via the control spring force. For example, the resistive features of the first and second hold detent features may be a high friction interface positioned on the outer surface of the collar and inner surface of the needle shroud and/or on the shroud pin such that when the resistive features meet after retraction of the needle shroud to the hold position, they add a resistive force and create the hold detent force. The resistive features are configured such that the resistive force can be overcome by the control spring force when the user releases the user hold force. The high friction interface may be a material interface with a high friction that activates the hold detent mechanism in the hold position to create the hold detent force. The material interface may be, without limitation, for example a crush rub interface in which the inherent stiffness of the material, which may be part of the collar and/or needle shroud or shroud pin, provides a contact force resulting in a friction force, which creates the hold detent force and assists in reducing the user hold force against the control spring force when the needle shroud and/or injection device is being maintained in the hold position. When the user hold force is released after the medicament has been delivered to the subject, then the control spring force overcomes the contact force/friction force caused by the material interface and the needle shroud extends to a final position or locked position such that the needle shroud has extended from the outer casing of the injection device and encloses the used needle. The needle shroud may be locked using a locking mechanism that prevents the needle shroud from retracting over the material interface to expose the used needle. In some embodiments, the locking mechanism may also be a high friction interface that is configured to retain the needle shroud in the final or locked position. Alternatively, or additionally, the high friction interface may be based on smaller-scale elastic deformation of the material of the collar, needle shroud or shroud pin, e.g., a small domed or convex feature on the collar which can "bump-off" and/or engage with a concavity feature on the opposing side of the needle shroud or shroud pin, respectively.

Figure 5:
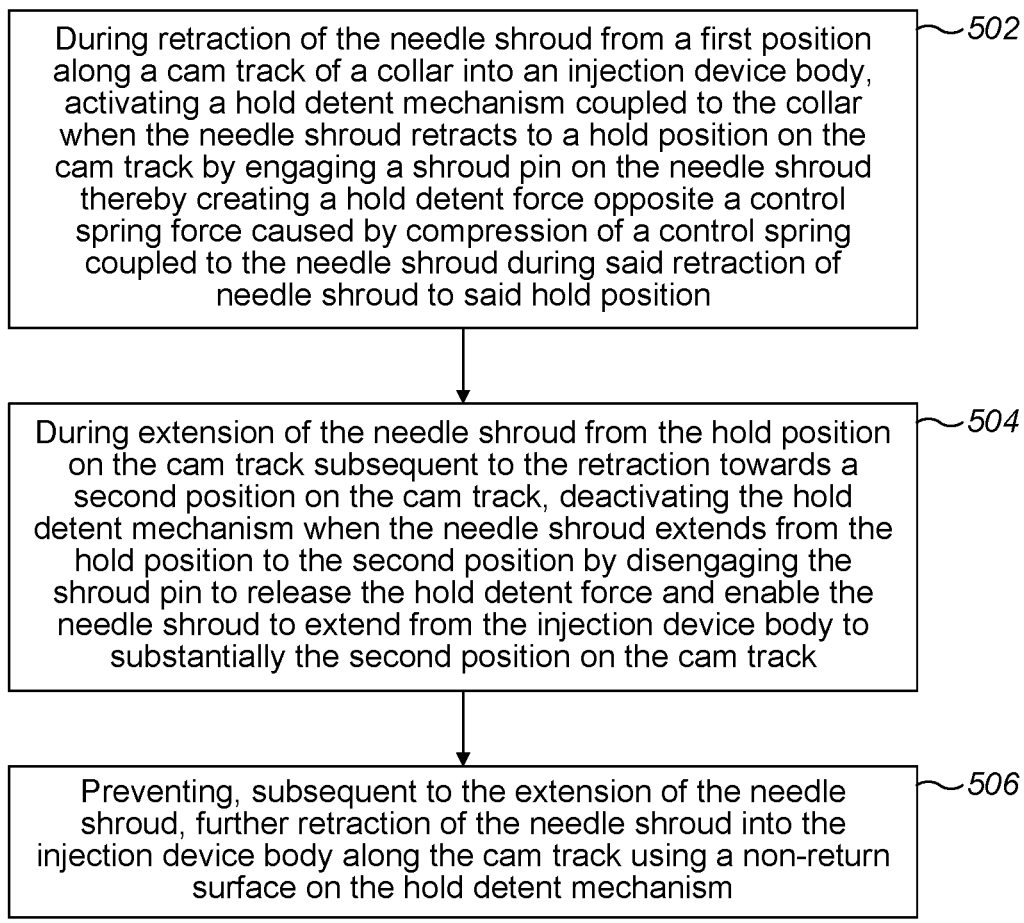
FIG. 5 shows a flow diagram of an example method of securing a needle shroud of an injection device.

FIG. 5 shows a flow diagram of an example method of operating a collar and needle shroud of an injection device with a hold detent mechanism. The method corresponds to the operations described in relation to FIGS. 2A to 3G.

At operation 502, during retraction of the needle shroud from a first position (or initial position) along a cam track of the collar into an injection device body, activating the hold detent mechanism coupled to the collar when the needle shroud retracts to a hold position on the cam track by engaging a shroud pin on the needle shroud thereby creating a hold detent force opposite a control spring force caused by compression of a control spring coupled to the needle shroud during said retraction of needle shroud to said hold position during retraction of the needle shroud from an initial position into an injection device body.

At operation 504, during extension of the needle shroud from the hold position on the cam track subsequent to the retraction towards a second position on the cam track, deactivating the hold detent mechanism when the needle shroud extends from the hold position to the second position by disengaging the shroud pin to release the hold detent force and enable the needle shroud to extend from the injection device body to substantially the second position on the cam track. The second position being a final or locked position.

In operation 506, preventing, subsequent to the extension of the needle shroud, further retraction of the needle shroud into the injection device body along the cam track using a non-return surface on the hold detent mechanism. The needle shroud has extended such that it encloses the needle of the injection device.

In some examples, subsequent to the extension of the needle shroud, further retraction of the needle shroud into the injection device body is prevented using the non-return surface of the hold detent mechanism of the collar. The non-return surface may comprise an angled edge and/or a rectangular shaped block that prevents the needle shroud from retracting into the outer casing and/or moving towards the hold position to expose the needle. When in the locked position or final position, the needle shroud is configured to enclose the needle, and is locked such that it does not expose the needle even if the needle shroud slightly retracts due to tolerances involved in locking the needle shroud to the final position or locked position.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides, and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively, or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly (A21), Arg (B31), Arg (B32) human insulin (insulin glargine); Lys (B3), Glu (B29) human insulin (insulin glulisine); Lys (B28), Pro (B29) human insulin (insulin lispro); Asp (B28) human insulin (insulin aspart); human insulin, wherein proline in position B28 is replaced by Asp, Lys, Leu, Val or Ala and wherein in position B29 Lys may be replaced by Pro; Ala (B26) human insulin; Des (B28-B30) human insulin; Des (B27) human insulin and Des (B30) human insulin.

Examples of insulin derivatives are, for example, B29-N-myristoyl-des (B30) human insulin, Lys (B29) (N-tetradecanoyl)-des (B30) human insulin (insulin detemir, Levemir®); B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des (B30) human insulin, B29-N-omega-carboxypentadecanoyl-gamma-L-glutamyl-des (B30) human insulin (insulin degludec, Tresiba®); B29-N—(N-lithocholyl-gamma-glutamyl)-des (B30) human insulin; B29-N—(ω-carboxyheptadecanoyl)-des (B30) human insulin and B29-N—(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrome. Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g., a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full-length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems, and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014(E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014(E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

Those of skill in the art will understand that modifications (additions and/or removals) of various components of the embodiments described herein may be made without departing from the full scope and spirit of the present invention, which encompass such modifications and any and all equivalents thereof.

LIST OF REFERENCE NUMBERS

100—injection device
102—outer casing/housing

102a—distal end of outer casing/housing
104—reservoir
106—plunger
108—collar
110—cap
112—longitudinal axis
114—rear casing
114a—rear shroud of the rear casing
114b—end stop of the rear shroud
116—needle
118—needle shroud/sleeve/cover
118a—distal end of needle shroud/sleeve/cover
120—control spring
122—drive spring
124—stopper
126—distal end
128—proximal end
200—injection device
202—outer casing of the injection device
204—needle shroud/sleeve/cover
206—rear casing
206a—rear casing shroud
206b—end stop of the rear casing shroud
208—collar
208a—flexible arm of collar
208b—non-flexible thick portion of flexible arm 208a
210—hold detent mechanism
210A—first hold detent feature
210B—second hold detent feature
212—control spring
214—control spring force
216—reservoir
218—needle
220—subject
222—reduced hold force
224—hold detent force
230—hold detent mechanism
230A—first hold detent feature
230B—second hold detent feature
231—longitudinal axis of the injection device or collar
232—ramped surface of first hold detent feature
234—distal end of the second hold detent feature 230B
236—ramped recess in rear shroud 206a
238—distance between distal end of second hold detent feature 230B and where ramped surface 232 intersects the flexible arm 208a
239—locking space
240—hold detent mechanism
240A—first hold detent feature
240B—second hold detent feature
242—ramped surface of second hold detent feature 240B
244—distal longitudinal direction
300—collar
301—longitudinal axis of the collar 300 or injection device
302—cam track
303—axial longitudinal direction
302A—first portion of cam track 302
302A-1—initial section of first portion 302A of cam track 302
302A-2—first angled section of first portion 302A of cam track 302
302B—second portion of cam track 302
302C—third portion of cam track 302
304A—first hold detent feature
305—second axial direction
306a—flexible arm of the first hold detent feature 304A
306b—ramped surface of the first hold detent feature 304A
306c—planar surface block of the first hold detent feature 304A
306d—distal end of the planar surface block 306c or distal end of first hold detent feature 304A or flexible arm 306a
306e—ramped wall of first hold detent feature 304A
307—rotational direction of collar 300
308A—initial position
308B—hold position
308B-1—activated hold position
308C—final or locked position
309—second axial longitudinal direction
310—hold detent mechanism
311—third axial longitudinal direction
312—needle shroud
314—shroud pin or second hold detent feature
324—wall of first portion 302A of cam track 302
324a—upper wall of angled section 302A-2 of first portion 302A of cam track 302
328—planar recess
402—Force profile of prior art device during insertion
404—Force profile of embodiments during insertion
406—Force profile of prior art device during removal
408a—Force profile of embodiments prior to activation of hold detent mechanism
408b—Force profile of embodiments at activation and during hold of hold detent mechanism
408c—Force profile of embodiments at peak hold detent force during hold of hold detent mechanism
410—Force profile of embodiments during removal
412—Force profile of embodiments during removal after hold detent mechanism deactivated

The invention claimed is:

1. An injection device comprising:
an injection device body;
a needle shroud retractable into the injection device body comprising a shroud pin;
a control spring coupled to the needle shroud and biased to cause the needle shroud to be at least partially extended from the injection device body in an initial position; and
a collar rotatable with respect to the injection device body and comprising a cam track engageable with the shroud pin;
a hold detent mechanism coupled to the cam track of the collar, wherein the hold detent mechanism is configured to:
activate, when the needle shroud is retracted from a first position on the cam track into the injection device body to a hold position on the cam track, by engaging the shroud pin thereby creating a hold detent force opposite a control spring force caused by compression of the control spring during said retraction of needle shroud to said hold position; and
deactivate, when the needle shroud is extracted from the hold position on the cam track subsequent to the retraction towards a second position on the cam track, by disengaging the shroud pin thereby releasing the hold detent force and enable the needle shroud to extend from the injection device body to the second position on the cam track; and
wherein the hold detent mechanism further comprises a non-return surface configured to, subsequent to the extension of the needle shroud, prevent further retraction of the needle shroud into the injection device body along the cam track towards the hold position.

2. The injection device of claim 1, wherein the hold detent mechanism comprises a hold detent feature coupled to the collar, which, when activated, interacts with the shroud pin for creating the hold detent force.

3. The injection device of claim 2, wherein the hold detent feature comprises at least one of:
   a flexible arm;
   a resilient clip;
   a high friction interface; and
   a partial cut-out or flap on the needle shroud.

4. The injection device of claim 1, wherein the cam track comprises:
   a first portion of the cam track configured to, during retraction of the needle shroud into the injection device body, guide the shroud pin from the first position to the hold position and cause the collar to rotate relative to the injection device body;
   a second portion of the cam track configured to, during extension of the needle shroud from the injection device body subsequent to the retraction, guide the shroud pin from the hold position to the second position;
   wherein the hold detent mechanism is positioned in a region of intersection between the first and second portions of the cam track, and is further configured to guide the shroud pin towards the hold position prior to activating.

5. The injection device of claim 4, wherein the hold detent feature comprises a first ramped wall surface for guiding the shroud pin from the first portion of the cam track to the second portion of the cam track towards the hold position.

6. The injection device of claim 5, wherein the hold detent feature comprises a second ramped contact surface that intersects with the first ramped wall surface and configured for engaging with the shroud pin in the region of intersection of the first and second portions of the cam track after needle shroud is retracted to the hold position and prior to retraction, wherein the hold detent mechanism activates by the second ramped contact surface engaging with at least a portion of the shroud pin causing a hold detent force in an opposite direction to the control spring force caused by compression of the control spring during retraction.

7. The injection device of claim 4, wherein when the needle shroud is extracted from the hold position subsequent to the retraction, the hold detent mechanism is deactivated by the control spring force overcoming the hold detent force in which the shroud pin is guided by the second portion of the cam track to pass over the second ramped contact face of the hold detent feature to create a biasing force on a portion of the hold detent feature that radially flexes the portion of the hold detent feature away from the shroud pin towards the longitudinal axis of the injection device body or collar enabling the control spring force to extract the needle shroud to substantially the second position.

8. The injection device of claim 7, wherein the portion of the hold detent feature that has a biasing force applied to radially flex away from the shroud pin towards the longitudinal axis of the injection device body or collar is the non-return surface of the hold detent feature, and when the shroud pin is guided along the second portion of the cam track past the non-return surface of the hold detent feature, the biassing force is released causing the portion of the hold detent feature to radially flex towards is original configuration, wherein the non-return surface when the hold detent feature is in the original configuration prevents further retraction of the needle shroud into the injection device body along the second portion of cam track towards the hold position.

9. The injection device of claim 2, wherein the first hold detent feature is coupled to the collar shroud by a snap fit; or
   wherein the first hold detent feature is integral to the collar and formed by a resilient partial cut-out of the collar.

10. The injection device of claim 1, wherein the hold detent force of the hold detent mechanism at least partially supports the needle shroud against the control spring force rather than the full control spring force being fully transferred to the user when the injection device is in the hold position.

11. The injection device of claim 1, wherein the control spring is a compression spring configured to bias the needle shroud towards an extended position.

12. The injection device of claim 1, wherein the injection device further comprises:
   a plunger and biasing means for biasing the plunger towards the distal end of the injection device, wherein:
   when the needle shroud is in the first position, the plunger is retained by a combination of the rear casing and the collar preventing the biasing means from displacing the plunger in the distal direction; and
   on activation of the injection device, the collar rotates and guides the shroud pin of the needle shroud to the holding position and causing, when the needle shroud is in the holding position, the biasing means to move the plunger in the distal direction of the injection device.

13. The injection device of claim 1, wherein the injection device further comprises a needle, and wherein the needle shroud is arranged to shroud the needle when in an extended position.

14. The injection device of claim 13, wherein the injection device further comprises a reservoir containing a medicament, the reservoir coupled to the plunger via a stopper at a distal portion of the reservoir and the reservoir coupled to the needle at a proximal end of the reservoir, and wherein, when the needle shroud moves into the holding position, the biasing means moves the plunger to displace the stopper in the distal direction causing the medicament stored in the reservoir to be expelled from the injection device via the needle.

15. The injection device of claim 1, further comprising at least two hold detent mechanisms equally spaced around the circumference of the collar.

16. A collar for an injection device comprising a cam track engageable with a shroud pin of a needle shroud and a hold detent mechanism coupled to the cam track of the collar, wherein:
   the needle shroud is retractable into the injection device body of the injection device, the injection device comprising a control spring coupled to the needle shroud and biased to cause the needle shroud to be at least partially extended from the injection device body in an initial position;
   the collar is rotatable in relation to the longitudinal axis of the injection device body; and
   the hold detent mechanism is configured to:
      activate, when the needle shroud is retracted from a first position on the cam track into the injection device body to a hold position on the cam track, by engaging the shroud pin thereby creating a hold detent force opposite a control spring force caused by compression of the control spring during said retraction of needle shroud to said hold position; and deactivate, when the needle shroud is extracted from the hold position on the cam track subsequent to the retraction towards a second position on the cam track, by disengaging the shroud pin thereby releasing the hold detent force and enable the needle shroud to extend from the injection device body to the second position on the cam track; and wherein the hold detent mechanism further comprises a non-return surface configured to, subsequent to the extension of the needle shroud, prevent further retraction of the needle shroud into the injection device body along the cam track towards the hold position.

17. The collar of claim 16, wherein the hold detent mechanism comprises a hold detent feature coupled to the collar, which, when activated, interacts with the shroud pin for creating the hold detent force.

18. The collar of claim 17, wherein the hold detent feature comprises at least one of:
 a flexible arm;
 a resilient clip;
 a high friction interface; and
 a partial cut-out or flap on the needle shroud.

19. The collar of claim 16, wherein the cam track comprises:
 a first portion of the cam track configured to, during retraction of the needle shroud into the injection device body, guide the shroud pin from the first position to the hold position and cause the collar to rotate relative to the injection device body;
 a second portion of the cam track configured to, during extension of the needle shroud from the injection device body subsequent to the retraction, guide the shroud pin from the hold position to the second position;
 wherein the hold detent mechanism is positioned in a region of intersection between the first and second portions of the cam track, and is further configured to guide the shroud pin towards the hold position prior to activating.

20. The collar of claim 19, wherein the hold detent feature comprises a first ramped wall surface for guiding the shroud pin from the first portion of the cam track to the second portion of the cam track towards the hold position.

21. The collar of claim 20, wherein the hold detent feature comprises a second ramped contact surface that intersects with the first ramped wall surface and configured for engaging with the shroud pin in the region of intersection of the first and second portions of the cam track after needle shroud is retracted to the hold position and prior to retraction, wherein the hold detent mechanism activates by the second ramped contact surface engaging with at least a portion of the shroud pin causing a hold detent force in an opposite direction to the control spring force caused by compression of the control spring during retraction.

22. The collar of claim 19, wherein when the needle shroud is extracted from the hold position subsequent to the retraction, the hold detent mechanism is deactivated by the control spring force overcoming the hold detent force in which the shroud pin is guided by the second portion of the cam track to pass over the second ramped contact face of the hold detent feature to create a biasing force on a portion of the hold detent feature that radially flexes the portion of the hold detent feature away from the shroud pin towards the longitudinal axis of the injection device body or collar enabling the control spring force to extract the needle shroud to substantially the second position.

23. The collar of claim 22, wherein the portion of the hold detent feature that has a biasing force applied to radially flex away from the shroud pin towards the longitudinal axis of the collar is the non-return surface of the hold detent feature, and when the shroud pin is guided along the second portion of the cam track past the non-return surface of the hold detent feature, the biassing force is released causing the portion of the hold detent feature to radially flex towards is original configuration, wherein the non-return surface when the hold detent feature is in the original configuration prevents further retraction of the needle shroud into the injection device body along the second portion of cam track towards the hold position.

24. The collar of claim 17, wherein the first hold detent feature is coupled to the collar shroud by a snap fit.

25. The collar of claim 17, wherein the first hold detent feature is integral to the collar and formed by a resilient partial cut-out of the collar.

26. The collar of claim 16, wherein the hold detent force of the hold detent mechanism at least partially supports the needle shroud against the control spring force rather than the full control spring force being fully transferred to the user when the injection device is in the hold position.

27. The collar of claim 16, wherein the control spring is a compression spring configured to bias the needle shroud towards an extended position.

* * * * *

UNITED STATES PATENT AND TRADEMARK OFFICE
CERTIFICATE OF CORRECTION

PATENT NO. : 12,274,872 B1
APPLICATION NO. : 18/620097
DATED : April 15, 2025
INVENTOR(S) : Alexander Hee-Hanson et al.

Page 1 of 1

It is certified that error appears in the above-identified patent and that said Letters Patent is hereby corrected as shown below:

In the Claims

In Column 35, Line 64, Claim 8, delete "biassing force" and insert -- biasing force --

In Column 38, Line 28 (approx.), Claim 23, delete "biassing force" and insert -- biasing force --

Signed and Sealed this
Twenty-second Day of July, 2025

Coke Morgan Stewart
*Acting Director of the United States Patent and Trademark Office*